US008440043B1

(12) United States Patent
Schneider et al.

(10) Patent No.: US 8,440,043 B1
(45) Date of Patent: May 14, 2013

(54) ABSORBENT ARTICLE PROCESS AND APPARATUS FOR INTERMITTENTLY DEACTIVATING ELASTICS IN ELASTIC LAMINATES

(75) Inventors: Uwe Schneider, Cincinnati, OH (US); Michael Brian Quade, Blue Ash, OH (US); Jose Angel Mercado, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/434,912

(22) Filed: Mar. 30, 2012

(51) Int. Cl.
*B29C 65/00* (2006.01)
*B32B 37/00* (2006.01)
*B32B 38/04* (2006.01)

(52) U.S. Cl.
USPC ........... 156/269; 156/250; 156/251; 156/257; 156/510; 156/516; 156/522; 156/160; 156/166; 156/176; 156/178; 156/179

(58) Field of Classification Search ............... 156/250, 156/252, 253, 256, 257, 264, 265, 229, 163, 156/164, 160, 161, 166, 176, 178, 179, 269, 156/510, 516, 522; 83/37, 314, 331, 339, 83/343, 346, 348, 505, 506
See application file for complete search history.

(56) References Cited

U.S. PATENT DOCUMENTS

| 167,309 A | 8/1875 | Daniels |
| 1,351,751 A | 9/1920 | Hoff |
| 3,083,757 A * | 4/1963 | Kraft et al. .................... 156/515 |
| 3,340,757 A | 9/1967 | Rudszinat |
| 3,736,659 A | 6/1973 | McLean |
| 3,753,397 A * | 8/1973 | Shrewsbury et al. ........... 99/491 |
| 3,821,837 A | 7/1974 | Faber |
| 3,823,634 A | 7/1974 | Rod et al. |
| 3,828,637 A | 8/1974 | Slack |
| 3,835,746 A | 9/1974 | Young, Jr. et al. |
| 3,848,594 A | 11/1974 | Buell |
| 3,860,003 A | 1/1975 | Buell |
| 3,957,569 A * | 5/1976 | Freitag .......................... 156/515 |
| 4,020,724 A | 5/1977 | Quinlan |
| 4,068,694 A | 1/1978 | Schnidt et al. |
| 4,081,301 A | 3/1978 | Buell |

(Continued)

FOREIGN PATENT DOCUMENTS

| CA | 2152328 C | 8/1996 |
| EP | 0 487 921 A2 | 6/1992 |

(Continued)

OTHER PUBLICATIONS

U.S. Appl. No. 13/434,984, filed Mar. 30, 2012, Uwe Schneider.

(Continued)

*Primary Examiner* — John Goff
*Assistant Examiner* — Hannuri L Kwon
(74) *Attorney, Agent, or Firm* — Charles R. Matson

(57) ABSTRACT

The present disclosure relates to methods and apparatuses for assembling absorbent articles, and more particularly, methods and apparatuses for severing elastic in an advancing elastic laminate. A continuous elastic laminate may be formed by bonding elastic strands between a first continuous substrate layer and a second continuous substrate layer. As discussed in more detail below, the continuous elastic laminate may advance through a cutting apparatus that intermittently deactivates or severs the elastic strands of the elastic laminate along the machine direction.

10 Claims, 21 Drawing Sheets

U.S. PATENT DOCUMENTS

| | | |
|---|---|---|
| 4,284,454 A | 8/1981 | Joa |
| 4,347,959 A | 9/1982 | Ivinger |
| 4,353,762 A | 10/1982 | Bouda |
| 4,425,173 A | 1/1984 | Frick |
| 4,479,836 A | 10/1984 | Dickover et al. |
| 4,483,228 A | 11/1984 | Waite et al. |
| 4,561,355 A | 12/1985 | Cuir et al. |
| 4,610,678 A | 9/1986 | Weisman et al. |
| 4,617,082 A | 10/1986 | Oshefsky et al. |
| 4,640,165 A | 2/1987 | McMahon et al. |
| 4,658,875 A | 4/1987 | Grabovac |
| 4,662,875 A | 5/1987 | Hirotsu et al. |
| 4,673,402 A | 6/1987 | Weisman et al. |
| 4,695,278 A | 9/1987 | Lawson |
| 4,699,033 A | 10/1987 | Gherardi |
| 4,699,622 A | 10/1987 | Toussant et al. |
| 4,704,115 A | 11/1987 | Buell |
| 4,743,144 A | 5/1988 | Shikata |
| 4,795,454 A | 1/1989 | Dragoo |
| 4,826,090 A | 5/1989 | Orphall |
| 4,834,735 A | 5/1989 | Alemany et al. |
| 4,846,815 A | 7/1989 | Scripps |
| 4,888,231 A | 12/1989 | Angstadt |
| 4,894,060 A | 1/1990 | Nestegard |
| 4,900,384 A | 2/1990 | Sanders et al. |
| 4,909,803 A | 3/1990 | Aziz et al. |
| 4,919,738 A | 4/1990 | Ball et al. |
| 4,920,843 A | 5/1990 | Strömberg et al. |
| 4,946,527 A | 8/1990 | Battrell |
| 4,962,683 A | 10/1990 | Scheffer et al. |
| 4,963,140 A | 10/1990 | Robertson et al. |
| 5,032,120 A | 7/1991 | Freeland et al. |
| 5,046,671 A | 9/1991 | Hughes |
| 5,064,489 A | 11/1991 | Ujimoto et al. |
| 5,086,683 A | 2/1992 | Steidinger |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,224,408 A * | 7/1993 | Steidinger .................. 83/674 |
| 5,242,436 A | 9/1993 | Weil et al. |
| 5,260,345 A | 11/1993 | DesMarais et al. |
| 5,271,442 A | 12/1993 | Carpenter et al. |
| 5,327,804 A | 7/1994 | Creaden |
| 5,342,338 A | 8/1994 | Roe |
| 5,357,836 A | 10/1994 | Strömberg et al. |
| 5,363,728 A | 11/1994 | Elsner et al. |
| 5,387,207 A | 2/1995 | Dyer et al. |
| 5,393,360 A | 2/1995 | Bridges et al. |
| 5,397,316 A | 3/1995 | LaVon et al. |
| 5,409,442 A | 4/1995 | Smithwick, Jr. |
| 5,499,978 A | 3/1996 | Buell et al. |
| 5,500,075 A | 3/1996 | Herrmann |
| 5,507,736 A | 4/1996 | Clear et al. |
| 5,525,175 A | 6/1996 | Blenke et al. |
| 5,554,145 A | 9/1996 | Roe et al. |
| 5,562,646 A | 10/1996 | Goldman et al. |
| 5,569,234 A | 10/1996 | Buell et al. |
| 5,580,411 A | 12/1996 | Nease et al. |
| 5,591,152 A | 1/1997 | Buell et al. |
| 5,599,335 A | 2/1997 | Goldman et al. |
| 5,622,581 A | 4/1997 | Ducker et al. |
| 5,628,097 A | 5/1997 | Benson et al. |
| 5,643,396 A | 7/1997 | Rajala et al. |
| 5,660,657 A | 8/1997 | Rajala et al. |
| 5,669,894 A | 9/1997 | Goldman et al. |
| 5,671,589 A | 9/1997 | Irvine et al. |
| 5,702,551 A | 12/1997 | Huber et al. |
| 5,707,330 A | 1/1998 | Kiamco et al. |
| 5,709,255 A | 1/1998 | Toogood |
| 5,745,922 A | 5/1998 | Rajala et al. |
| 5,775,194 A | 7/1998 | Spada |
| 5,916,661 A | 6/1999 | Benson et al. |
| 6,004,306 A | 12/1999 | Robles et al. |
| 6,026,727 A | 2/2000 | Meeks |
| 6,107,539 A | 8/2000 | Palumbo et al. |
| 6,120,487 A | 9/2000 | Ashton |
| 6,131,627 A | 10/2000 | Zaiser |
| 6,217,690 B1 | 4/2001 | Rajala et al. |
| 6,248,097 B1 | 6/2001 | Beitz et al. |
| 6,248,195 B1 | 6/2001 | Schmitz |
| 6,279,444 B1 | 8/2001 | Kellner et al. |
| 6,319,347 B1 | 11/2001 | Rajala et al. |
| 6,432,098 B1 | 8/2002 | Kline et al. |
| 6,460,439 B2 | 10/2002 | Belanger |
| 6,481,318 B1 | 11/2002 | Kinigakis et al. |
| 6,482,278 B1 | 11/2002 | McCabe et al. |
| 6,545,197 B1 | 4/2003 | Muller et al. |
| 6,546,987 B1 | 4/2003 | Tachibana et al. |
| 6,554,815 B1 | 4/2003 | Umebayashi |
| 6,602,374 B2 * | 8/2003 | Gunther et al. ............... 156/192 |
| 6,641,692 B2 | 11/2003 | Reynolds et al. |
| 6,705,981 B2 | 3/2004 | Bergeron et al. |
| 6,711,824 B2 | 3/2004 | Hruska |
| 6,790,798 B1 | 9/2004 | Suzuki et al. |
| 6,811,019 B2 | 11/2004 | Christian et al. |
| 7,001,477 B2 | 2/2006 | Saraf |
| 7,171,884 B2 | 2/2007 | De Torre |
| 7,171,885 B1 | 2/2007 | Obiol |
| 7,189,031 B2 | 3/2007 | Bellinger et al. |
| 7,192,422 B2 | 3/2007 | Otsubo |
| 7,214,175 B2 | 5/2007 | Janzen |
| 7,220,251 B2 | 5/2007 | Otsubo et al. |
| 7,329,245 B2 | 2/2008 | Torigoshi et al. |
| 7,383,865 B2 | 6/2008 | Umebayashi et al. |
| 7,435,309 B2 | 10/2008 | Komatsu |
| 7,530,972 B2 | 5/2009 | Ando et al. |
| 7,569,039 B2 | 8/2009 | Matsuda et al. |
| 7,587,966 B2 | 9/2009 | Nakakado et al. |
| 7,708,849 B2 | 5/2010 | McCabe |
| 7,771,407 B2 | 8/2010 | Umebayashi |
| 7,777,094 B2 | 8/2010 | Mori et al. |
| 7,832,435 B1 | 11/2010 | Lui |
| 7,861,756 B2 * | 1/2011 | Jenquin et al. ............... 156/496 |
| 7,900,542 B2 | 3/2011 | Kapolnek |
| 7,954,681 B2 | 6/2011 | Smith et al. |
| 8,092,440 B2 | 1/2012 | Hermansson et al. |
| 8,142,590 B2 | 3/2012 | Rajala et al. |
| 8,196,500 B2 | 6/2012 | Mansfield et al. |
| 8,312,797 B2 | 11/2012 | Hsu |
| 2001/0023343 A1 | 9/2001 | Mizutani et al. |
| 2002/0046802 A1 | 4/2002 | Tachibana et al. |
| 2002/0173764 A1 | 11/2002 | Takino et al. |
| 2002/0184985 A1 | 12/2002 | Ishibuchi et al. |
| 2003/0089447 A1 | 5/2003 | Molee et al. |
| 2003/0135189 A1 | 7/2003 | Umebayashi |
| 2004/0097895 A1 | 5/2004 | Busam et al. |
| 2004/0158212 A1 | 8/2004 | Ponomarenko et al. |
| 2004/0243083 A1 | 12/2004 | Matsuda et al. |
| 2005/0107764 A1 | 5/2005 | Matsuda et al. |
| 2008/0028902 A1 * | 2/2008 | Baggot et al. ................. 83/13 |
| 2009/0145276 A1 | 6/2009 | Scheck et al. |
| 2009/0283207 A1 * | 11/2009 | Tachibana et al. ............ 156/209 |
| 2009/0312730 A1 | 12/2009 | LaVon et al. |
| 2010/0101392 A1 | 4/2010 | Zeuschner |
| 2010/0167896 A1 | 7/2010 | Hada et al. |
| 2010/0221496 A1 | 9/2010 | de Jong |
| 2010/0305532 A1 | 12/2010 | Ashton et al. |
| 2011/0125122 A1 | 5/2011 | Thorson et al. |
| 2012/0021186 A1 | 1/2012 | Schneider |
| 2012/0061015 A1 | 3/2012 | LaVon et al. |
| 2012/0061016 A1 | 3/2012 | LaVon et al. |
| 2012/0095429 A1 | 4/2012 | Kobayashi et al. |
| 2012/0247681 A1 | 10/2012 | Yamamoto |

FOREIGN PATENT DOCUMENTS

| | | |
|---|---|---|
| EP | 0 626 161 A1 | 11/1994 |
| EP | 1 188 427 B1 | 3/1999 |
| EP | 1 078 620 A2 | 2/2000 |
| EP | 1 260 206 B1 | 6/2005 |
| EP | 1 961 404 B1 | 8/2008 |
| JP | 63-116293 U | 1/1987 |
| JP | 63-144995 | 9/1988 |
| JP | 09-299398 A | 11/1997 |
| JP | 11-347988 | 12/1999 |

| | | |
|---|---|---|
| JP | 3545210 B | 1/2000 |
| JP | 4090158 B | 3/2001 |
| JP | 2001-121471 | 5/2001 |
| JP | 4630352 B | 8/2008 |

OTHER PUBLICATIONS

U.S. Appl. No. 13/435,036, filed Mar. 30, 2012, Uwe Schneider.
U.S. Appl. No. 13/435,063, filed Mar. 30, 2012, Gary Dean LaVon.
U.S. Appl. No. 13/435,247, filed Mar. 30, 2012, Uwe Schneider.
U.S. Appl. No. 13/435,503, filed Mar. 30, 2012, Tina Brown.
U.S. Appl. No. 13/434,984, filed Mar. 30, 2012—Office Action mailed Dec. 21, 2012, (7 pages).
U.S. Appl. No. 13/435,036, filed Mar. 30, 2012—Office Action mailed Jan. 2, 2013, (9 pages).
U.S. Appl. No. 13/435,063, filed Mar. 30, 2012—Office Action mailed Jan. 3, 2013, (8 pages).
U.S. Appl. No. 13/435,247, filed Mar. 30, 2012—Office Action mailed Jan. 4, 2013, (9 pages).
U.S. Appl. No. 13/435,503, filed Mar. 30, 2012—Office Action mailed Jan. 10, 2013, (5 pages).

* cited by examiner

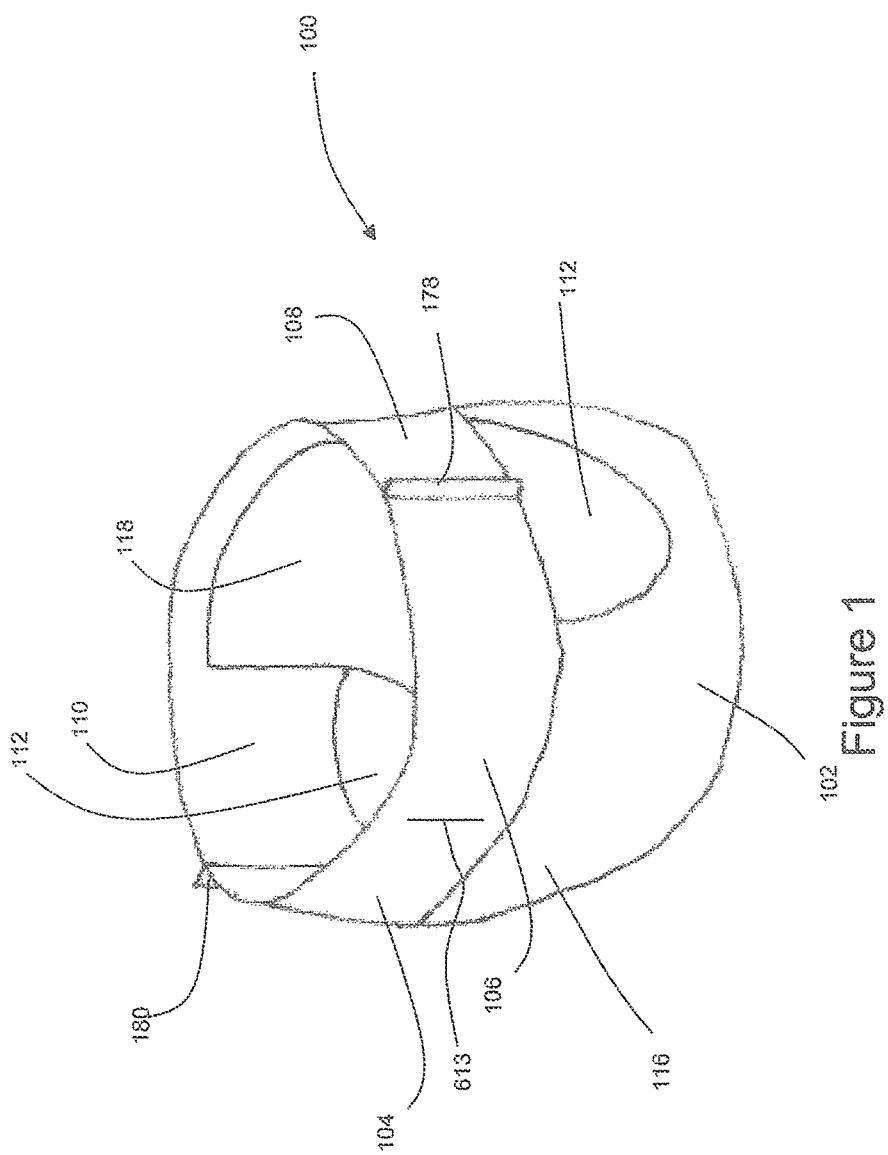

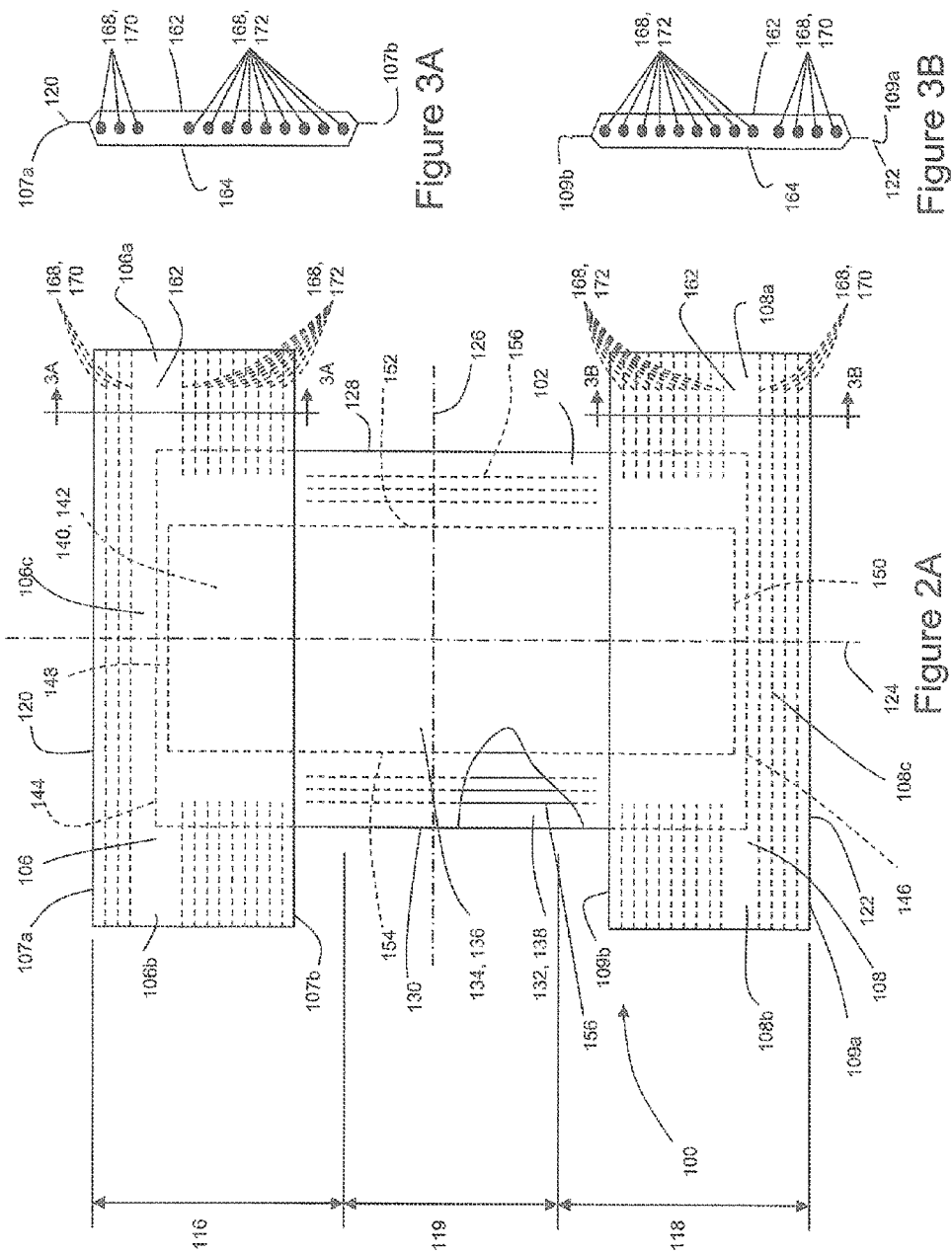

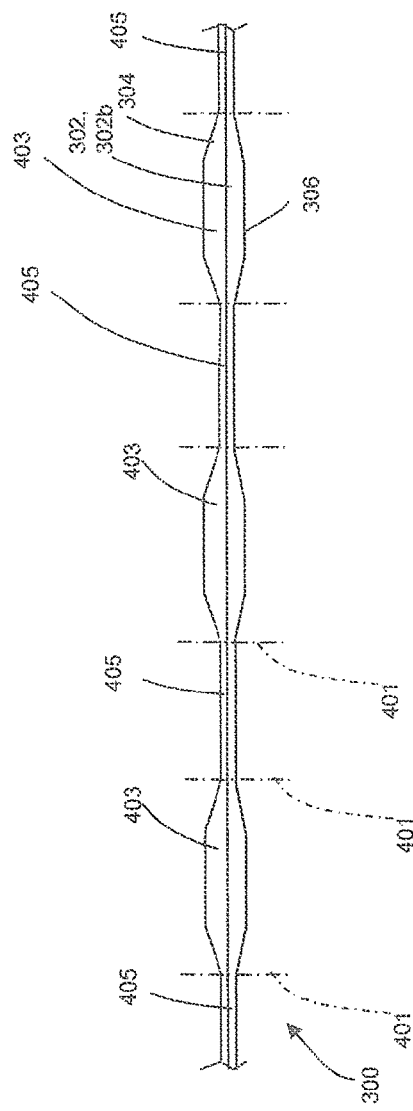
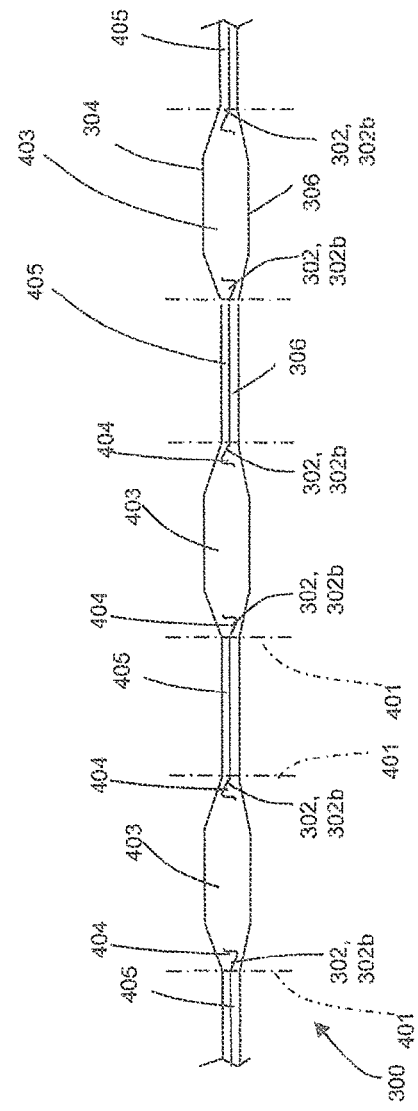

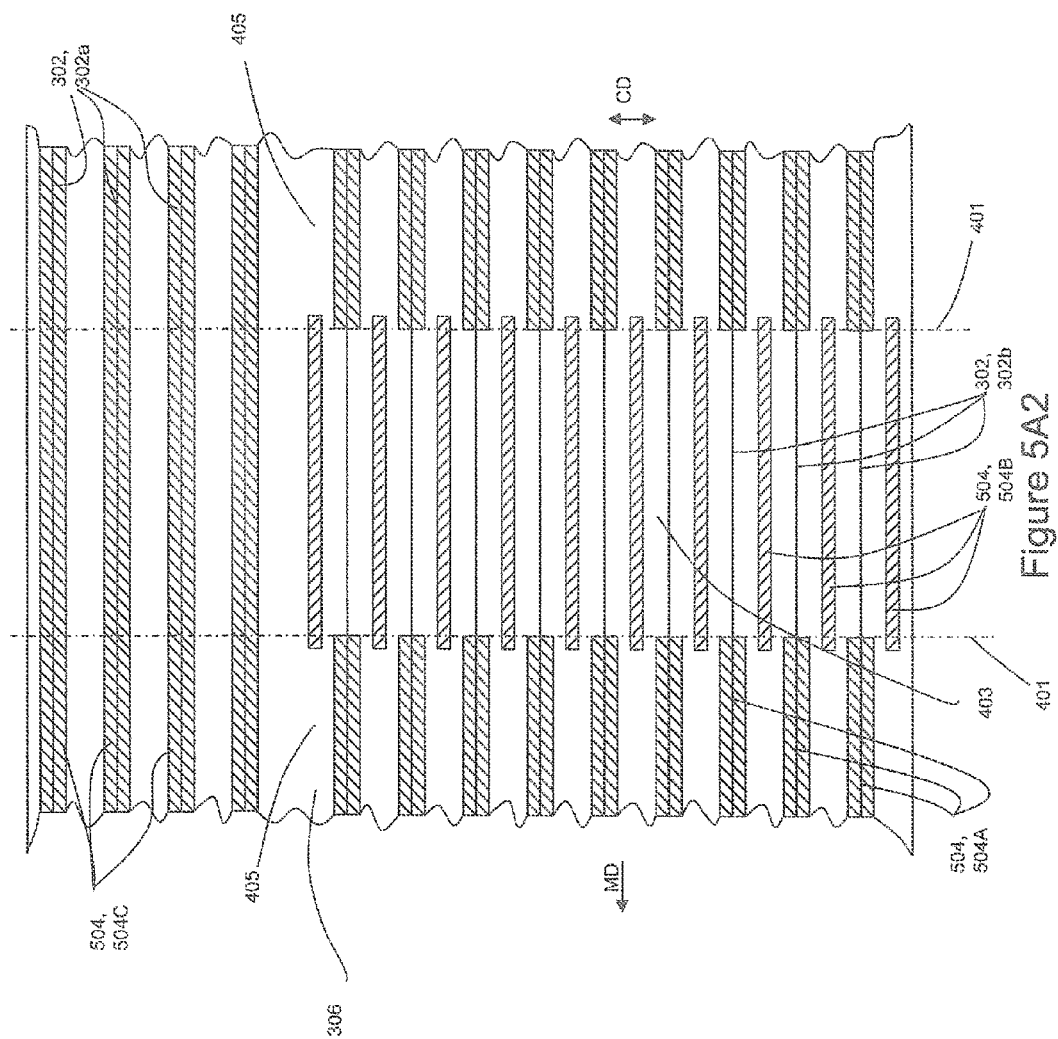

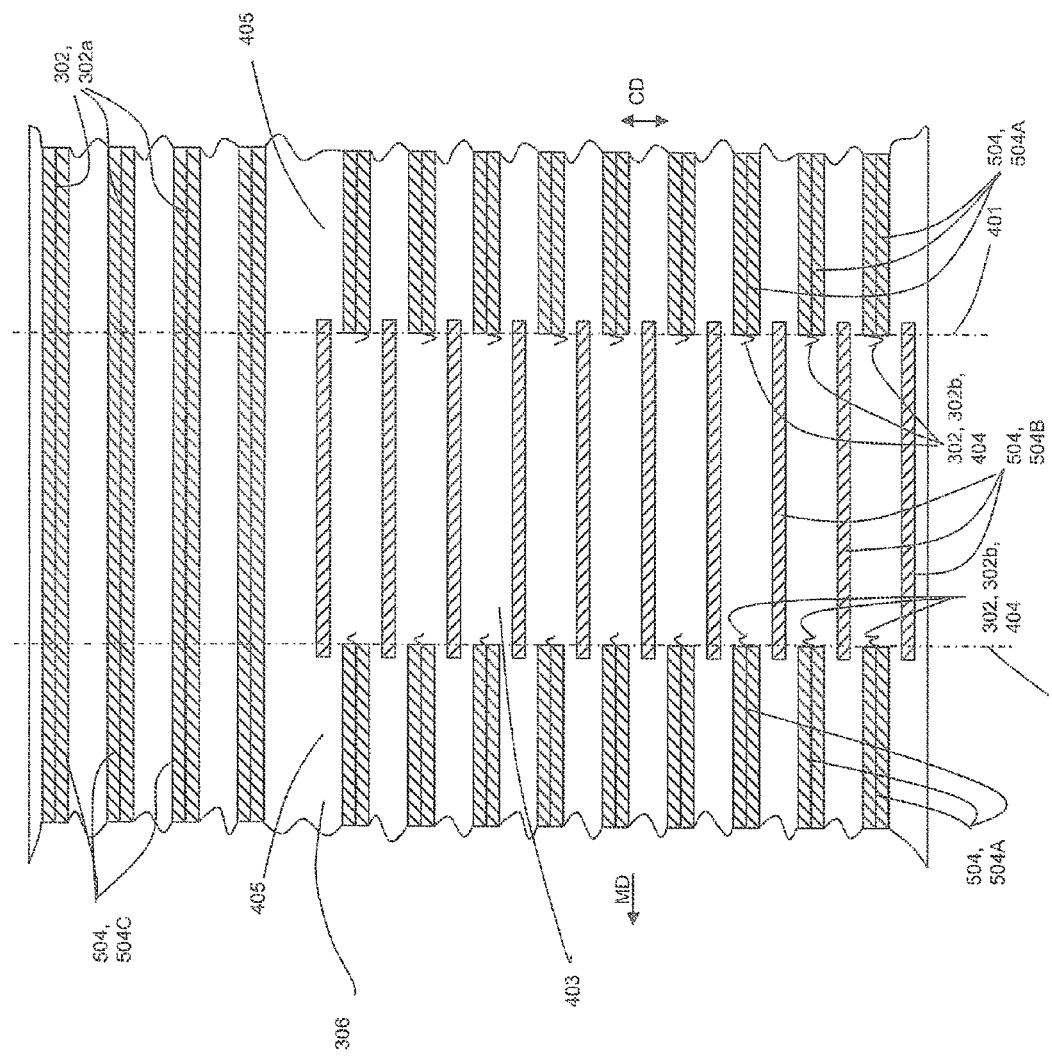

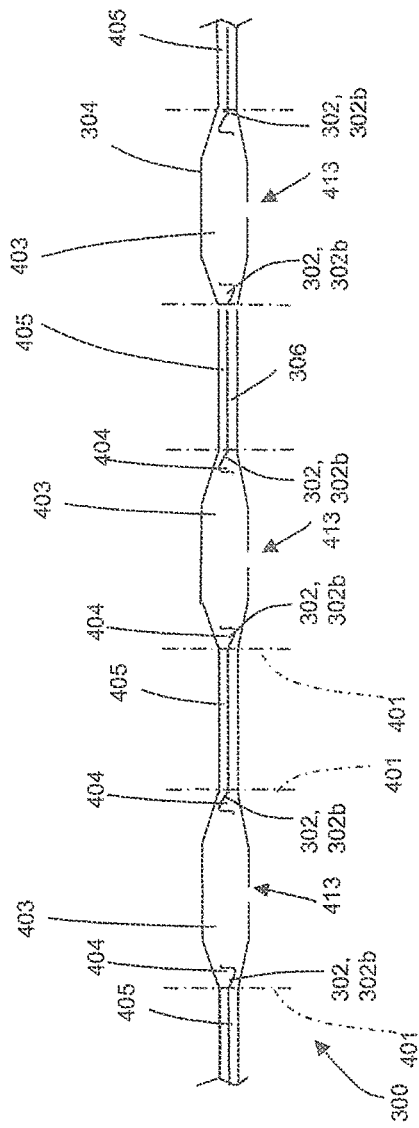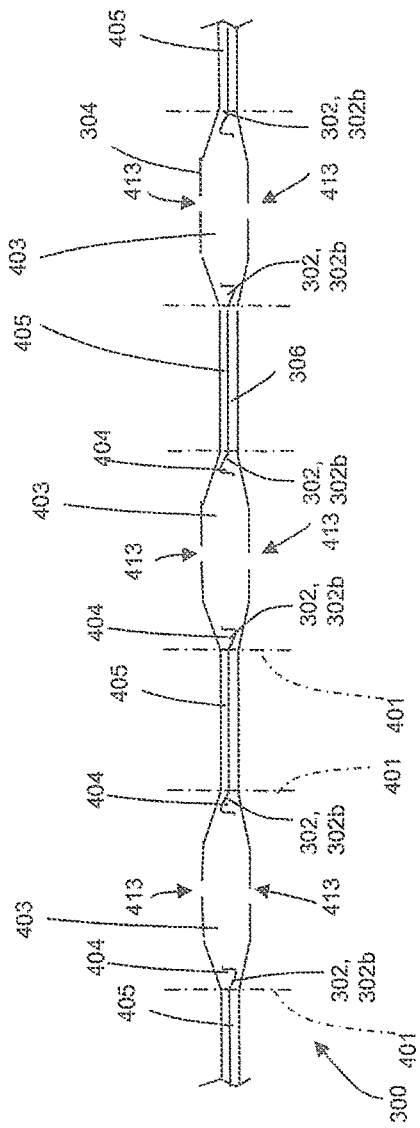

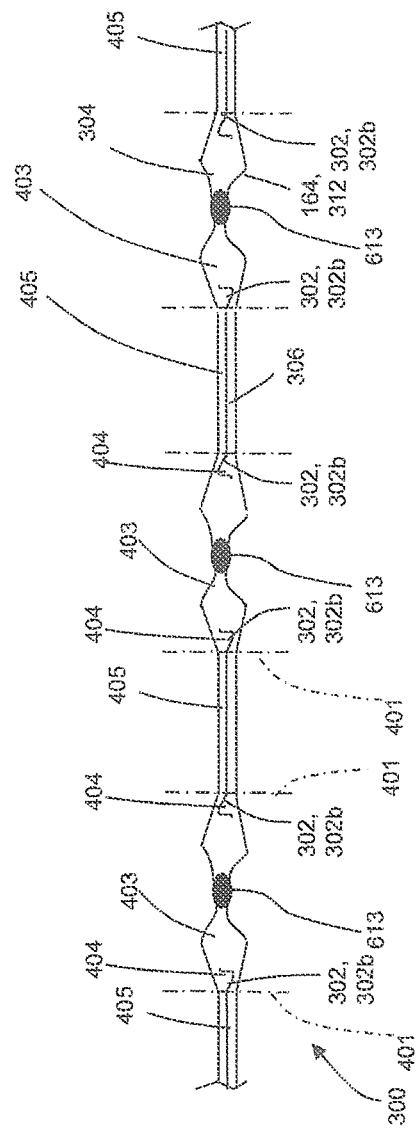
Figure 5B1C

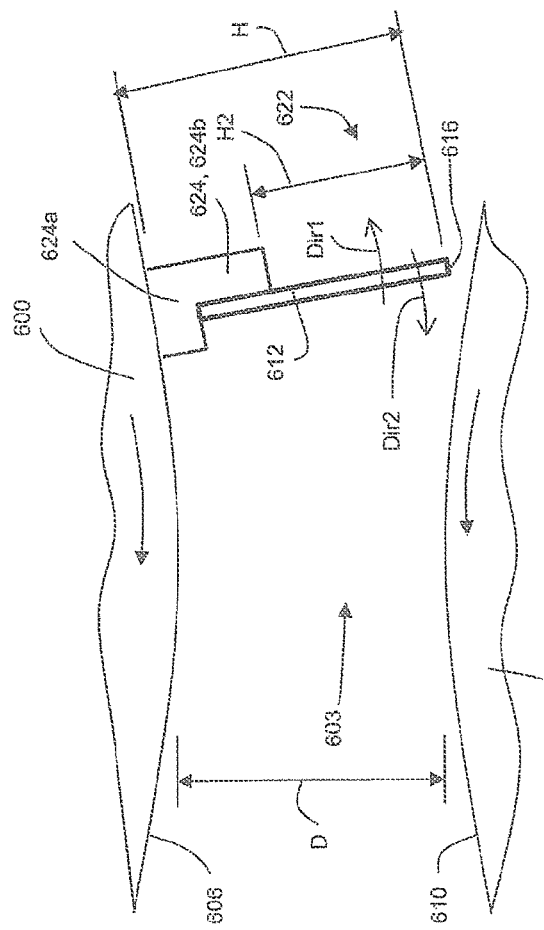
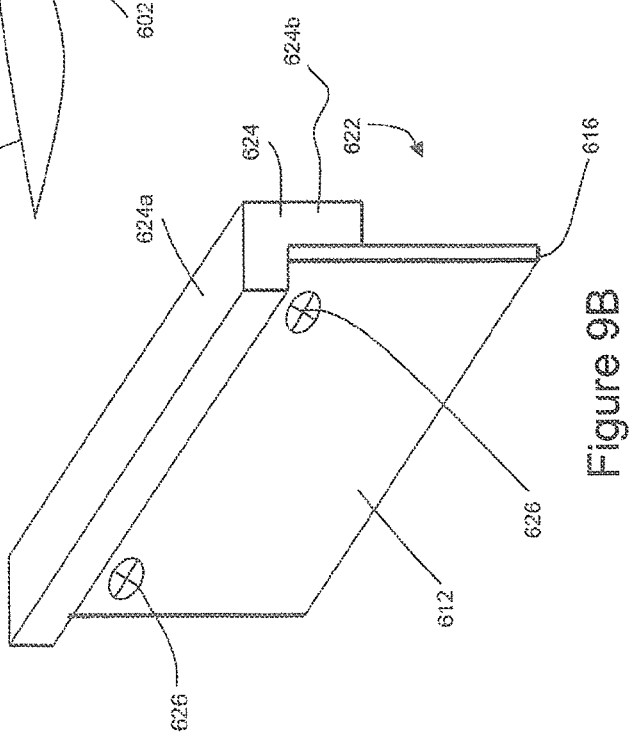

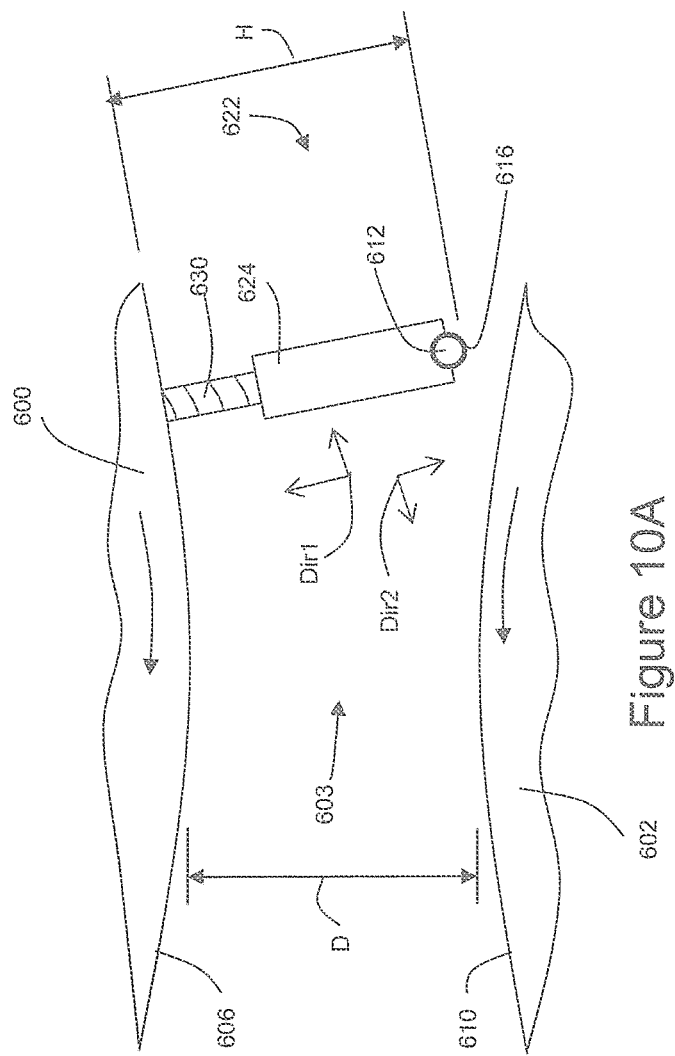

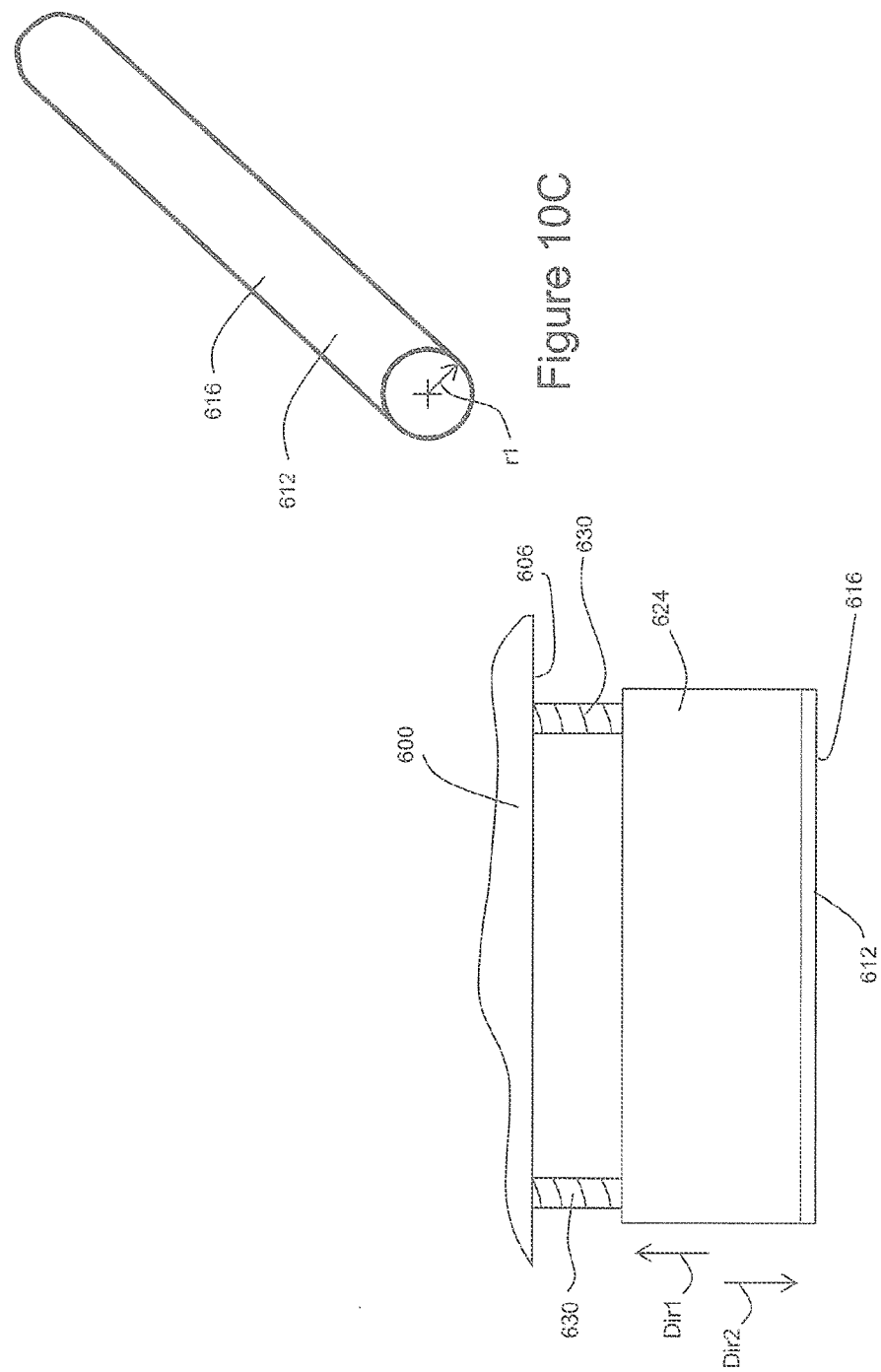

ABSORBENT ARTICLE PROCESS AND APPARATUS FOR INTERMITTENTLY DEACTIVATING ELASTICS IN ELASTIC LAMINATES

FIELD OF THE INVENTION

The present disclosure relates to apparatuses and methods for manufacturing absorbent articles, and more particularly, methods and apparatuses for deactivating elastic in an advancing laminate.

BACKGROUND OF THE INVENTION

Along an assembly line, various types of articles, such as for example, diapers and other absorbent articles, may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheet, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

Various methods and apparatuses may be used for attaching different components to the advancing web and/or otherwise modify the advancing web. Some production operations are configured to construct elastic laminates including elastics bonded with the one or more substrates advancing in a machine direction. The operations may be further configured to cut and/or otherwise deactivate discrete lengths of the elastics. In some operations, an elastic laminate may advance through a cutting station that cuts the elastic in the advancing laminate. However, some current configurations have certain drawbacks. For example, some present cutting apparatuses may cause unintended damage to the elastic laminate, such as by severing the substrate while cutting the elastic. In addition, the blades on some current cutting apparatuses may be susceptible to wear after relatively short operating periods. Such blade wear may manifest itself in inconsistent elastic cutting. Further, it may be relatively expensive to repair worn cutting devices. Consequently, it would be beneficial to provide elastic cutting methods and apparatuses that are configured to provide relatively consistent cutting of elastics without excessive and/or unintentional damage to the substrate. It would also be beneficial to provide elastic cutting methods and apparatuses that are less susceptible to blade wear and that may be configured for ease of repair at relatively low costs.

SUMMARY OF THE INVENTION

The present disclosure relates to methods and apparatuses for assembling absorbent articles, and more particularly, methods and apparatuses for severing elastic in an advancing elastic laminate. A continuous elastic laminate may be formed by bonding elastic strands between a first continuous substrate layer and a second continuous substrate layer. As discussed in more detail below, the continuous elastic laminate may advance through a cutting apparatus that intermittently deactivates or severs the elastic strands of the elastic laminate along the machine direction.

In one form, a method for severing elastic strands in an elastic laminate includes the steps of: advancing a continuous first substrate layer and a continuous second substrate layer in a machine direction; stretching an elastic strand in the machine direction; bonding the stretched elastic strand between the first substrate layer and the second substrate layer to form a continuous elastic laminate; advancing the elastic laminate in the machine direction through a nip defined between a cutting roll and an anvil roll, the cutting roll rotating around a first axis of rotation and the anvil roll rotating around a second axis of rotation, wherein the anvil roll includes an outer circumferential surface defining a minimum distance D1 between the outer circumferential surface and first axis of rotation, wherein the cutting roll includes a blade having a distal edge defining a maximum distance D2 between the distal edge and the first axis of rotation, and wherein the D2 is greater than D1; deflecting the distal edge of the blade by an interference distance, wherein the interference distance is equal to or greater than a difference between D2 and D1; and severing the elastic strand by pressing the distal edge of the blade against the elastic laminate in the nip.

In another form, an apparatus for severing elastic strands in an elastic laminate includes: an anvil roll including an outer circumferential surface; a cutting roll adjacent the anvil roll to define a nip between the anvil roll and the cutting roll, the cutting roll adapted to rotate about a first axis of rotation, wherein the outer circumferential surface and first axis of rotation are separated by a minimum distance D1; a blade connected with the cutting roll, the blade having a distal edge, and wherein the distal edge and the first axis of rotation are separated by a distance D2, wherein D2 is greater than D1 and defining an interference distance equal to the difference between D2 and D1; and wherein the distal edge of the blade is adapted to deflect the interference distance when moving through the nip.

BRIEF DESCRIPTION OF THE DRAWINGS

FIG. 1 is a perspective view of a diaper pant.

FIG. 2A is a partially cut away plan view of the diaper pant shown in FIG. 1.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 5A1 is a cross-sectional view of the elastic laminate from FIG. 5A taken along line A1-A1.

FIG. 5A2 shows a detailed view of a belt substrate with the first substrate layer cut-away.

FIG. 5B1 is a cross-sectional view of the elastic laminate from FIG. 5B taken along line B1-B1 showing elastics cut in non-bonded regions.

FIG. 5B2 shows a detailed view of the belt substrate from FIG. 5B with the first substrate layer cut-away to illustrate elastics after having been cut in the non-bonded regions.

FIG. 5B1A is a cross-sectional view of the elastic laminate from FIG. 5B taken along line B1-B1 showing elastics and first substrate layer cut in non-bonded regions.

FIG. 5B1B is a cross-sectional view of the elastic laminate from FIG. 5B taken along line B1-B1 showing elastics, the first substrate layer, and the second substrate layer cut in non-bonded regions.

FIG. 5B1C is a cross-sectional view of the elastic laminate from FIG. 5B taken along line B1-B1 with the first substrate layer and the second substrate layer bonded together by the cutting device.

FIG. 9A is a detailed side view of a cutting apparatus and an embodiment of a blade assembly.

FIG. 9B is a detailed isometric view of the blade assembly of FIG. 9A.

FIG. 10A is a detailed side view of a cutting apparatus and an embodiment of a blade assembly.

FIG. 10B is a side view of the blade assembly of FIG. 10A.

FIG. 10C is an isometric view of an embodiment of a blade having a cylindrical shape.

DETAILED DESCRIPTION OF THE INVENTION

Figure 2B:
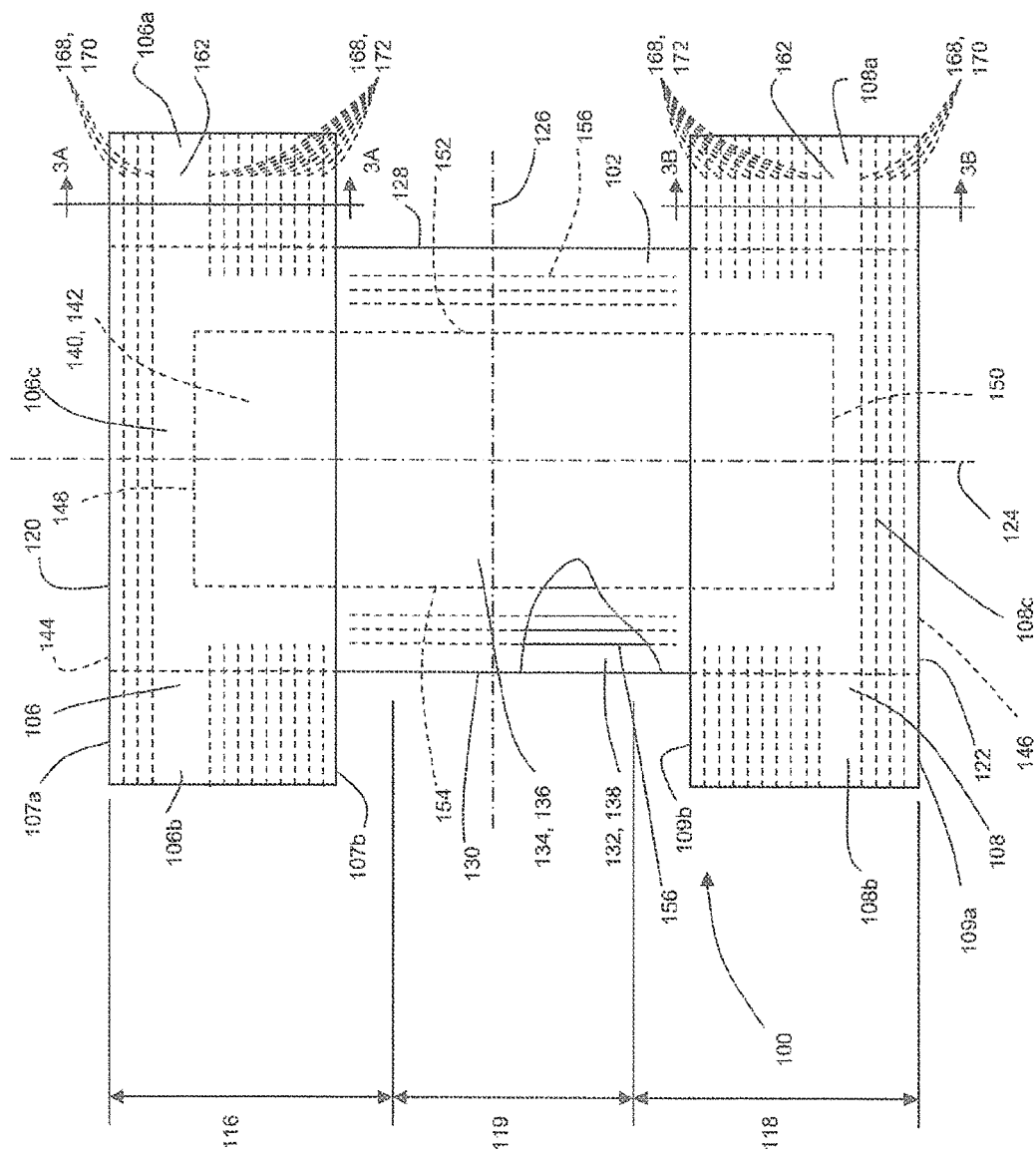
FIG. 2B is a partially cut away plan view of a second embodiment of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed.

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The present disclosure relates to methods and apparatuses for assembling absorbent articles, and more particularly, methods and apparatuses for severing elastic in an advancing elastic laminate. A continuous elastic laminate may be formed by bonding elastic strands between a first continuous substrate layer and a second continuous substrate layer. It is to be appreciated the elastic laminate can be formed in various ways. For example, in some embodiments, the first continuous substrate layer may be formed from a first continuous substrate, and the second continuous substrate layer may be formed from a second continuous substrate. In other embodiments, the first continuous substrate layer and the second continuous substrate layer may be formed by a folding portion of a single continuous substrate onto another portion of the single continuous substrate. As discussed in more detail below, the continuous elastic laminate may advance through a cutting apparatus that intermittently deactivates or severs the elastic strands of the elastic laminate along the machine direction.

In some embodiments, the elastic laminate may include the elastic strands that are intermittently bonded between substrate layers along the machine direction. As such, the elastic laminate may include bonded regions and non-bonded regions intermittently spaced along the machine direction, wherein the elastic strands are bonded to either the first substrate layer or the second substrate layer in bonded regions, and wherein the elastic strands are not bonded to either the first substrate layer or the second substrate layer in the non-bonded regions. The elastic strands may then be intermittently deactivated by severing the strands in the non-bonded regions of the continuous elastic laminate. As such the elastic laminate may include elastic regions and deactivated regions, wherein the elastic regions of the elastic laminate correspond with the bonded regions. And the deactivated regions of the elastic laminate may correspond with the non-bonded regions.

The processes and apparatuses discussed herein may be used to assemble elastic laminates in various types of substrate configurations, some of which may be used in the manufacture of different types of absorbent articles. To help provide additional context to the subsequent discussion of the process embodiments, the following provides a general description of absorbent articles in the form of diapers that may include elastic laminates that may be assembled in accordance with the methods and apparatuses disclosed herein. Although the methods and apparatuses herein are discussed below in the context of manufacturing absorbent articles, it is to be appreciated that the assembly methods and apparatuses herein may be configured to manufacture various types of substrates having intermittently spaced elastic and inelastic regions.

FIGS. 1 and 2A show an example of a diaper 100 that may include elastic laminates assembled in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 120 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 120 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 120 in the front waist region 116 and the laterally extending back waist edge 122 in the back waist region 118. When the diaper pant 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562, 646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795, 454; 4,704,115; 4,909,803; and U.S. Patent Publication No. 2009/0312730A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172.

As shown in FIG. 2A, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2A, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

As previously mentioned, the apparatuses and methods according to the present disclosure may be utilized to assemble elastic laminates 300 used in various components of absorbent articles, such as for example, elastic belts 106, 108 and/or leg cuffs 156. Although the following methods may be provided in the context of the diaper 100 shown in FIGS. 1 and 2A, it is to be appreciated that elastic laminates can be used with various embodiments of diapers manufactured according the methods disclosed herein, such as for example, the absorbent articles disclosed in U.S. Pat. No. 7,569,039, filed on Nov. 10, 2004; U.S. Patent Publication No. 2005/0107764A1, filed on Nov. 10, 2004; U.S. patent application Ser. No. 13/221,127, filed on Aug. 30, 2011; and U.S. patent application Ser. No. 13/221,104, filed on Aug. 30, 2011, which are all hereby incorporated by reference herein.

Figure 4:
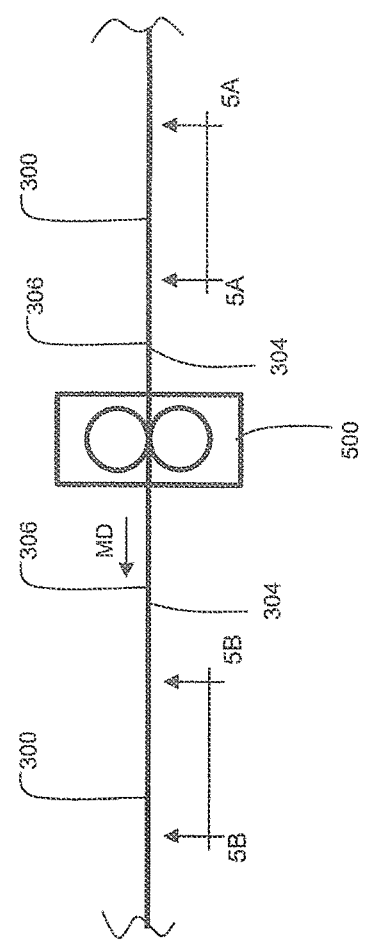
FIG. 4 is a schematic side view of a cutting apparatus adapted to sever elastics in an advancing elastic laminate.

FIG. 4 shows a schematic view of a cutting apparatus 500 adapted to sever elastic strands 302 in a continuous elastic laminate 300 advancing in a machine direction MD. It is to be appreciated that the cutting apparatus 500 may be adapted to cut elastics 302 in various different configurations of elastic laminates 300. For example, with reference to FIGS. 4, 5B, 5B1, and 5B2, the continuous elastic laminate 300 entering the cutting apparatus 500 may include a first substrate layer 304, a second substrate layer 306, and elastic strands 302 bonded between the first substrate layer 304 and the second substrate layer 306. In one example, the elastic laminate 300 may correspond with the elastic belts 106, 108 discussed above. Thus, the first substrate layer 304 may correspond with the inner layer 162; the second substrate layer may correspond with the outer layer 164; and the elastics 302 may correspond with the elastics 168, 170, 172 discussed above. As previously mentioned, the first continuous substrate layer 304 may be formed from a first continuous substrate, and the second continuous substrate layer 306 may be formed from a second continuous substrate. In some embodiments, the first continuous substrate layer 304 and the second continuous substrate layer 306 may be formed by a folding portion of a single continuous substrate onto another portion of the single continuous substrate, sandwiching the elastics 302 therebetween.

Figure 5A:
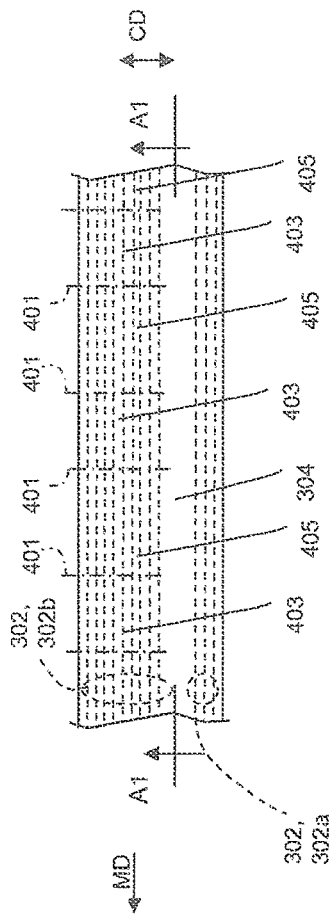
FIG. 5A is a view of the elastic laminate from FIG. 4 taken along line 5A-5A.
Figure 5B:
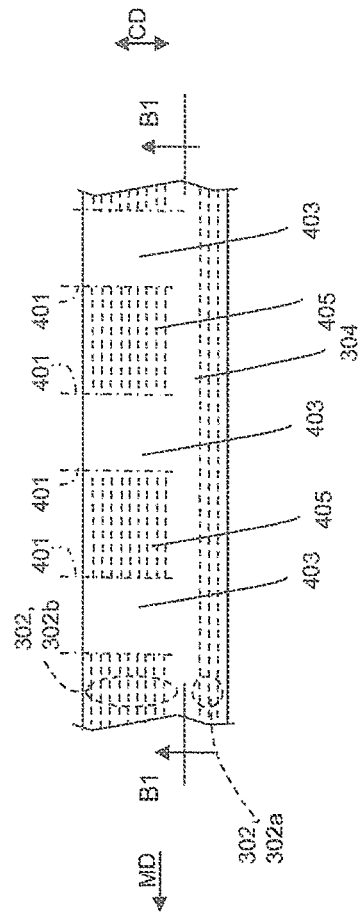
FIG. 5B is a view of continuous the advancing elastic laminate from FIG. 4 taken along line 5B-5B.

As shown in FIGS. 4 and 5A, the elastic laminate 300 may include first elastic strands 302a and second elastic strands 302b that are stretched in the machine direction MD and bonded with the first substrate layer 304 and/or the second substrate layer 306. More particularly, the first elastic strands 302a may be continuously bonded with the first substrate layer 304 and/or the second substrate layer 306 with adhesive along the machine direction MD. And the second elastic strands 302b may be intermittently bonded with the first substrate layer 304 and/or the second substrate layer 306 with adhesive along the machine direction MD. Thus, as shown in FIG. 5A, the elastic laminate 300 may include non-bonded regions 403 intermittently spaced between bonded regions 405 along the machine direction MD. Thus, the second elastic strands 302b are not bonded to either the first substrate layer 304 or the second substrate layer 306 in the non-bonded regions 403. And the second elastic strands 302b are bonded to the first substrate layer 304 and/or second substrate layer 306 in the bonded regions 405. For the purposes of clarity, dashed lines 401 are shown in FIGS. 5A, 5B, and others to represent example boundaries between the non-bonded regions 403 and the bonded regions 405. It is to be appreciated that such boundaries between the non-bonded regions 403 and the bonded regions 405 can also be curved, angled, and/or straight. As discussed in more detail below with reference to FIGS. 5A2 and 5B2, although the second elastic strands 302b are not bonded to the either the first substrate layer 304 or the second substrate layer 306 in the non-bonded regions 403, adhesive 504 may be applied in areas between the individual second elastic strands 172 to bond the first substrate layer 304 and second substrate layer 306 together in the non-bonded regions 403.

As shown in FIG. 4, the elastic laminate 300 advances in the machine direction MD to the cutting unit 500. The cutting unit 500 then intermittently deactivates the elastics 302 in the elastic laminate 300. More particularly, the cutting unit 500 may sever, cut, and/or break the second elastics 302b in the non-bonded regions 403 of the elastic laminate 300. As shown in FIGS. 5B, 5B1, and 5B2, severed ends 404 of the second elastics 302b retract or snap back to the bonded regions 405 of the elastic laminate 300. In some embodiments, such as shown in FIG. 5B1, the cutting unit 500 may be configured to sever only the elastics 300b in the non-bonded regions 403 of the elastic laminate without cutting through either the first substrate layer 304 or the second substrate layer 306. In other configurations, the cutting unit 500 may be configured to cut the elastics 302b in the non-bonded regions 403 of the elastic laminate 300 while also cutting through one or both the first substrate layer 304 and the second substrate layer 306. For example, FIG. 5B1A shows a configuration where the cutting unit 500 cuts slits 413 through the second substrate layer 306 while cutting the elastics 302b in the non-bonded regions 403 of the elastic laminate 300, without cutting through the first substrate layer 304. In another example, FIG. 5B1B shows a configuration where the cutting unit 500 cuts slits 413 through both the second substrate layer 306 and the first substrate layer 304 while cutting the elastics 302b in the non-bonded regions 403 of the elastic laminate 300.

As previously discussed, the second elastic strands 302b are not bonded to the either the first substrate layer 304 or second substrate layer 306 in the non-bonded regions 403. However, it is to be appreciated that the non-bonded regions 403 and bonded regions 405 may be configured with various adhesive applications. For example, in some configurations, the first substrate layer 304 and the second substrate layer 306 may not be bonded together in the non-bonded regions 403. In some configurations, adhesive may be applied to bond the first substrate layer 304 and the second substrate layer 306 together in the non-bonded regions 403. For example, FIG. 5A2 shows a detailed view of an elastic laminate 300 with the first substrate layer 306 cut-away to illustrate an embodiment of adhesive application in the bonded regions 405 and the non-bonded regions 403. More particularly, FIG. 5A2 shows an example adhesive application configuration wherein adhesive 504A has been applied to the first and second substrate layers 304, 306 and/or elastics 302b in the bonded regions 405, and wherein adhesive 504B has been applied either or both substrate layers 304, 306, and not the elastics 302b, in the non-bonded regions 403. As such, adhesive 504A may be intermittently applied along the machine direction MD in the bonded regions 405, and adhesive 504B may be intermittently applied along the machine direction in the non-bonded regions 403. Further, as shown in FIGS. 5A2 and 5B2, adhesive 504C may be continuously applied to the substrate layers 304, 306 and/or elastics 300a in the bonded regions 405 and non-bonded regions 403.

With continued reference to FIG. 5A2, adhesive 504A may be applied in strips along the elastics 302b extending the machine direction MD in the bonded regions 405. As such, the adhesive 504A bonds the first substrate layer 304, the second substrate layer 306, and the elastics 302b together in the bonded regions 405. In addition, adhesive 504B may be applied in strips between the elastics 302b extending the machine direction MD in the non-bonded regions 403. As such, the adhesive 504B bonds the first substrate layer 304 and the second substrate layer 306 together in the non-bonded regions 403. Further, strips of the adhesive 504B do not bond the elastics 302b to either the first substrate layer 304 or the second substrate layer 306 in the non-bonded regions 403. FIG. 5B2 shows a detailed view of the elastic laminate 300 from FIG. 5A2 with the first substrate layer 304 cut-away to illustrate the elastics 302b after having been cut in the non-bonded regions 403 wherein the severed ends 404 of the elastics 302b have retracted or snapped back to the bonded regions 405. As such, the elastic laminate 300 may include elastic regions 405a and deactivated regions 403a, wherein the elastic regions 405a of the elastic laminate 300 may correspond with the bonded regions 405. And the deactivated regions 403a of the elastic laminate 300 may correspond with the non-bonded regions 403.

Although an example elastic laminate 300 is described herein that may include elastic strands 302 intermittently bonded to define non-bonded regions 403 and bonded regions 405, it is to be appreciated that the apparatuses and methods herein may be configured to sever elastic strands 302 in other types of elastic laminate configurations. For example, some elastic laminates 300 may include elastic strands 302 continuously bonded with a first substrate layer 304 and a second substrate layer 306, and the cutting apparatus may sever the continuously bonded elastic strands 302 intermittently along the machine direction MD to define elastic regions 405a separated by deactivated regions 403a. More particularly, the elastic strands 302 may be intermittently deactivated by cutting the elastic strands 302 into one or more discrete pieces to define the deactivated regions 403a of the elastic laminate 300. In other examples, the cutting units 500 and methods herein may be configured to operate cut elastics in accordance with the methods and apparatuses disclosed in U.S. Patent Application entitled "APPARATUSES AND METHODS FOR MAKING ABSORBENT ARTICLES", filed on Mar. 30, 2012, which may be further identified by U.S. Patent Application entitled "APPARATUSES AND METHODS FOR MAKING ABSORBENT ARTICLES", filed on Mar. 30, 2012, which may be further identified by U.S. Patent Application entitled "APPARATUSES AND METHODS FOR MAKING ABSORBENT ARTICLES", filed on Mar. 30, 2012, which may be further identified by U.S. Patent Application entitled "APPARATUSES AND METHODS FOR MAKING ABSORBENT ARTICLES", filed on Mar. 30, 2012, which may be further identified by U.S. Patent Application entitled "METHODS AND APPARATUSES FOR MAKING LEG CUFFS FOR ABSORBENT ARTICLES", filed on Mar. 30, 2012, all of which are incorporated by reference herein.

Figure 6:
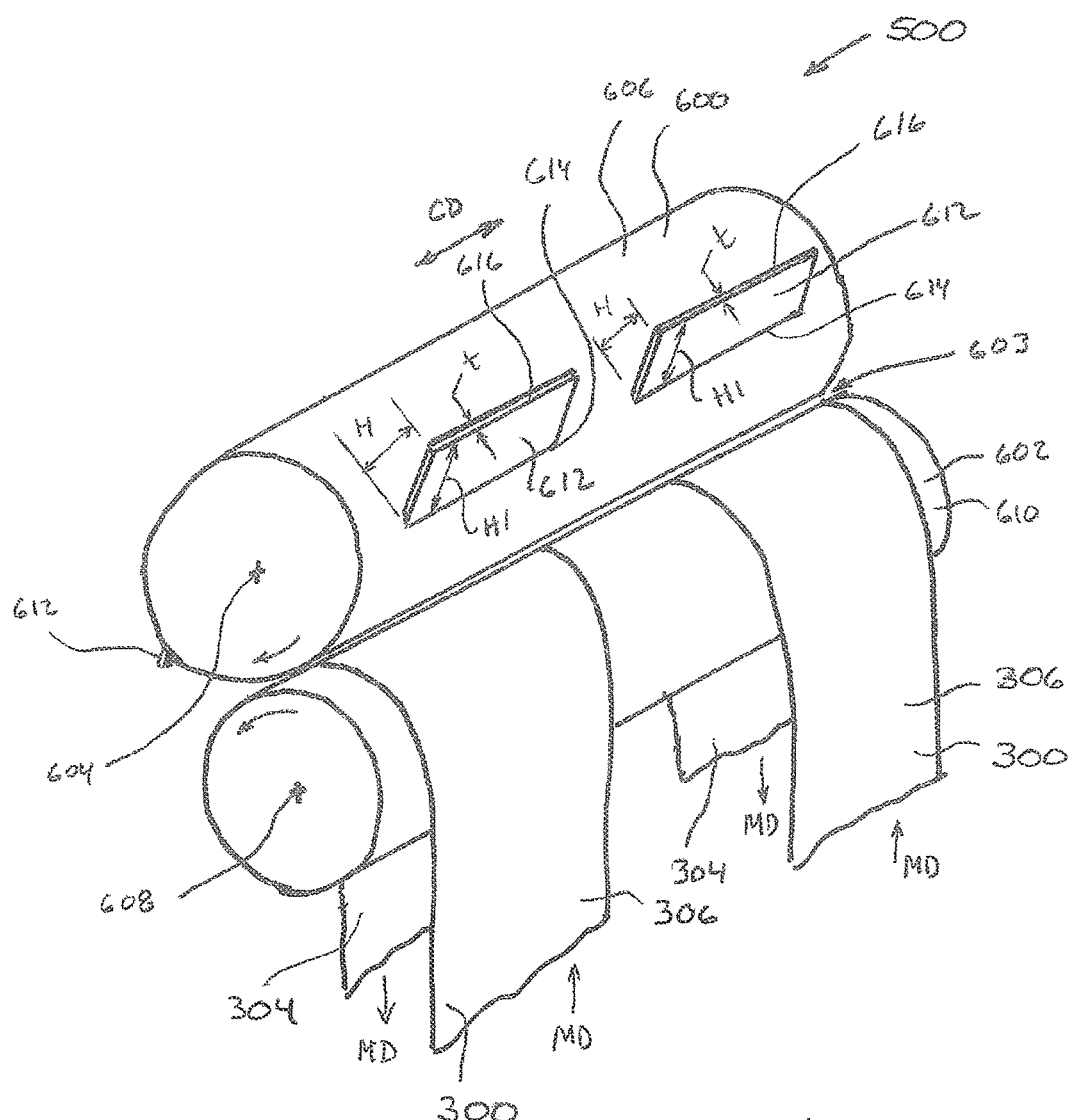
FIG. 6 is a perspective view of an embodiment of a cutting apparatus.
Figure 7:
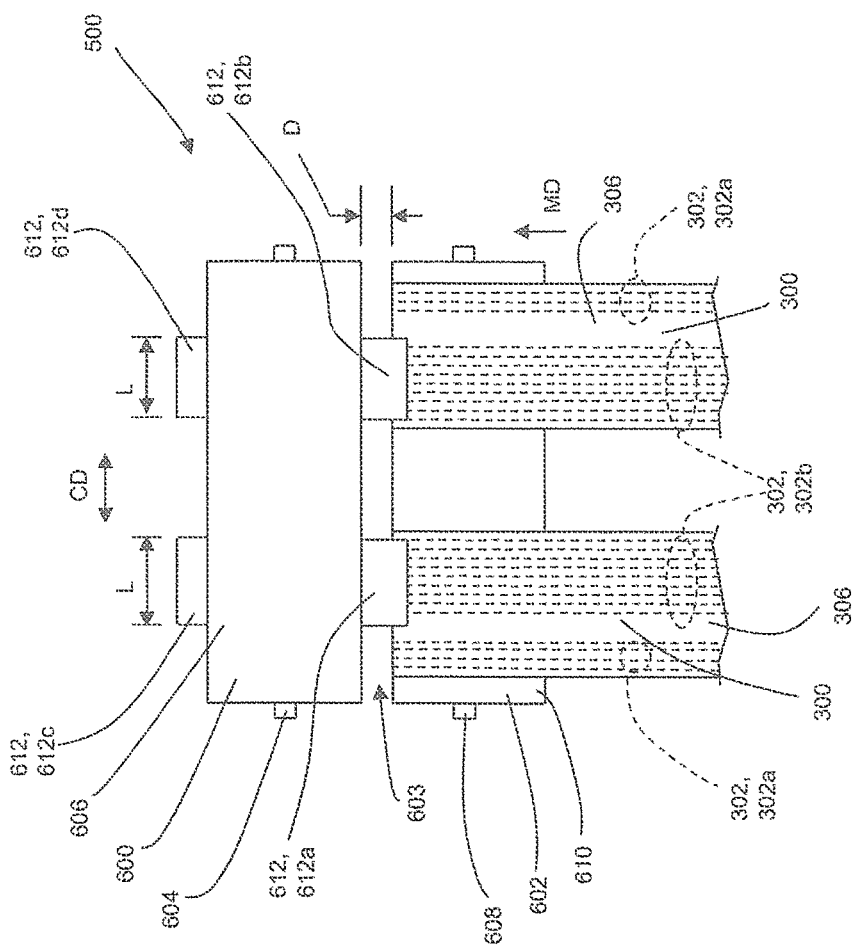
FIG. 7 is a front side view of the cutting apparatus of FIG. 6 as two blades are rotated toward two substrates partially wrapped around an anvil roll.

It is to be appreciated that various configurations of cutting units 510 can be used with the apparatuses and methods herein. For example, the cutting units may be configured with a flexible cutting blade arrangement. FIGS. 6 and 7 show an example embodiment of a cutting unit 500 including a cutting roll 600 and an anvil roll 602. The cutting roll 600 is adapted to rotate around an axis of rotation 604 and defines an outer circumferential surface 606. And the anvil roll 602 is adapted to rotate around an axis of rotation 608 and defines an outer circumferential surface 610. The cutting roll 600 is adjacent to the anvil roll 602 and create a nip 603 defined by a minimum distance, D, between the outer circumferential surface 606 of the cutting roll 602 and the outer circumferential surface 610 of the anvil roll 602. As shown in FIGS. 6 and 7, the cutting roll 600 may also include one or more blades 612. Each blade 612 may have a proximal end portion 614 extending in a cross direction (CD) a length, L, along the outer circumferential surface 606 of the cutting roll 600. The blades 612 may define a dimension, H1, extending from the proximal end portion 614 to a distal edge 616. In addition, from the proximal end portion 614, the blades may extend radially outward from the outer circumferential surface 606 of the cutting roll 600 to the distal edge 616 by a distance, H. It is to be appreciated that the blades 612 may extend radially outward from the outer circumferential surface 606 to define an angle of 90 degrees or less, such as about 45 degrees, between the blade 612 and a tangential plane intersecting the proximal end portion 614 on the outer circumferential surface 606. As such, in some embodiments, H1 may be equal to H, and in some embodiments, H1 may be greater than H. As shown in FIGS. 6 and 7, the blades 612 may define a rectangular shape having a first surface 618 and an opposing second surface 620 separated by a thickness, t. The blades 612 may have a small thickness, t, relative to the distance, H1, such that blades 612 are flexible or bendable.

Figures 8A, 8B, 8C:
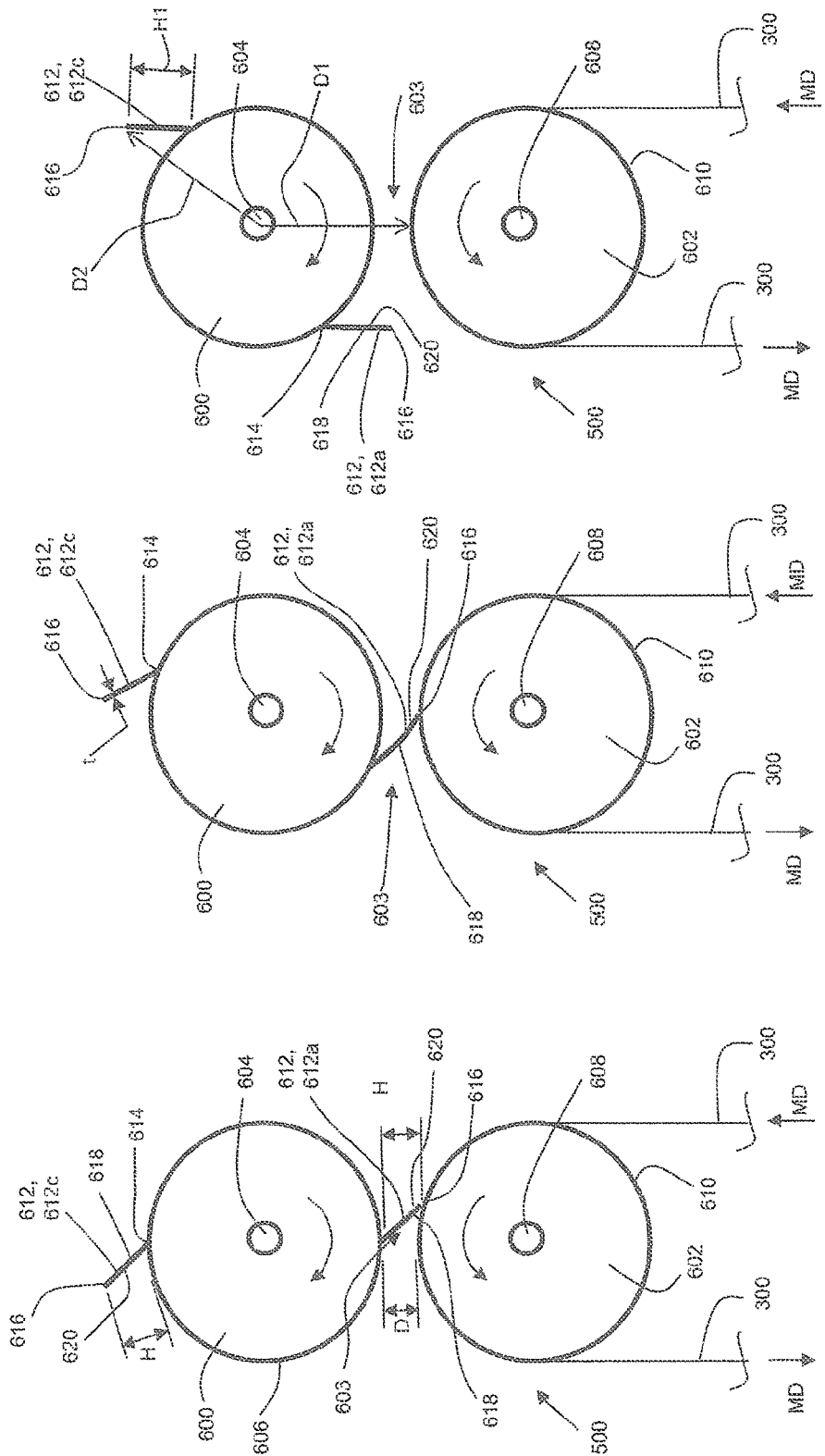
FIG. 8A is a left side view of the cutting apparatus of FIG. 7 showing the blade initiating contact with the substrate partially wrapped around the anvil roll.
FIG. 8B shows the cutting apparatus of FIG. 8A as the blade flexes while being rotated into contact with the substrate partially wrapped around the anvil roll.
FIG. 8C shows the cutting apparatus of FIG. 8B after the blade is rotated away from the substrate partially wrapped around the anvil roll.

As shown in FIGS. 6-8C, the cutting unit 500 may be arranged such that the first and second elastic laminates 300 advance in a machine direction MD to partially wrap around the outer circumferential surface 610 of the anvil roll 602. As the anvil roll 602 and the cutting roll 600 rotate, portions of the first surfaces 618 and the distal edges 616 of the blades 612 are moved into contact with the elastic laminates 300, such as shown in FIG. 8A. As shown in FIGS. 8A-8C, the distance, H, of each blade 612 is greater than the distance, D, between the cutting roll 600 and the anvil roll 602. Thus, with reference to FIG. 8B, as the blades 612 rotate though the nip 603 between the cutting roll 600 and the anvil roll 602, the blades 612 flex or bend inward along the second surface 620. As such, portions of the first surfaces 618 and/or the distal edges 616 of the blades 612 exert pressure on the elastic laminates 300 to sever the elastics 302, such as for example, elastics 302b in non-bonded regions 403 discussed above. Referring now to FIG. 8C, as the cutting roll 600 continues to rotate, the blades 612 move away from the nip 603 and straighten back out along the distance, H1, thus returning to the original blade shapes before entering the nip 603.

It is to be appreciated that the elastic laminates 300 may be arranged in various ways on the cutting unit 500. For example, as shown in FIGS. 6-8C, the elastic laminates 300 may advance in the machine direction MD to partially wrap around the rotating anvil roll 602 such that the first substrate layer 304 is in contact with the outer circumferential surface 610 of the anvil roll 602. As such, the blades 612 of the rotating cutting roll 600 contact the second substrate layers 306 of the elastic laminates 300 while advancing through the nip 603. It is to be appreciated that the elastic laminates 300 may be arranged such that either the first substrate layer 304 or the second substrate layer 306 is in contact with the outer circumferential surface 610 of the anvil roll 602. For example, in some embodiments, the elastic laminates 300 may be arranged to partially wrap around the rotating anvil roll 602 such that the first substrate layer 304 are in contact with the outer circumferential surface 610 of the anvil roll 602. As discussed above, the cutting unit 500 shown in FIGS. 6-8C may be configured to sever only the elastics 302b in the non-bonded regions 403 of the elastic laminates 300 without cutting through either the first substrate layer 304 or the second substrate layer 306. In other configurations, the cutting unit 500 may be configured to cut the elastics 302b in the non-bonded regions 403 of the elastic laminates 300 while also cutting through one or both the first substrate layer 304 and the second substrate layer 306.

As discussed above, the blades 612 of the cutting unit 500 exert pressure on the elastic laminates 300 to sever the elastics 302. In some embodiments, the pressure exerted by the blades 612 may also create a pressure bond between the first substrate layer 303 and the second substrate layer 306. For example, in embodiments wherein the first and second substrate layers 302, 306 comprise the outer layer belt material 162 and the inner layer belt material 164, both including nonwoven webs, the distal edges 616 of the blades 612 may exert enough pressure on the nonwoven webs to melt and fuse some of the nonwoven fibers together, thus creating a bond 613 between the outer layer belt material 162 and the inner layer belt material 164. Embodiments of the bond 613 are shown in FIG. 5B1C. A shown in FIG. 1, the bond 613 may be visible in the elastic belt 104 of the diaper 100, and may correspond with a shape of the distal edge 616 of the blade 612.

It is to be appreciated that the cutting unit 500 may be configured with various quantities of blades having various shapes and orientations. For example, the cutting unit 500 shown in FIGS. 6-8C includes four blades 612a, 612b, 612c, 612d. The first and second blades 612a, 612b may be located 180 degrees apart from the third and fourth blades 612c, 612d on the outer circumferential surface 606 of the cutting roll 600. It is to be appreciated that the cutting roll may also be configured with various numbers of blades arranged circumferentially along the outer circumferential surface 606 of the cutting roll 600. The proximal end portions 614 of the first blade 612a and the second blade 612b may also be aligned with each other and with the axis of rotation 604 so as to extend in a straight line in the cross direction (CD) perpendicular to the machine direction (MD). Similarly, proximal end portions 614 of the third blade 612c and the fourth blade 612d may be aligned with each other and with the axis of rotation 604 so as to extend in a straight line in the cross direction (CD) perpendicular to the machine direction (MD). In addition, the first blade 612a and the second blade 612b, as well as the third and fourth blades 612c, 612d, may define different lengths, L, and may separated from each other by various distances in the cross direction CD. For example, the lengths, L, of the blades 612 are configured such so as to engage portions of the elastic laminates 300 so as to cut the elastics 300b without cutting elastics 300a. In addition, the blades 612 may be configured to cut the elastics 300b simultaneously in the CD direction along a substantially straight line. It is also to be appreciated that the cutting roll 600 may be configured with more than or less than two blades 612 aligned along the CD direction of outer circumferential surface 606 of the cutting roll 600. For example, in some embodiments, instead of having the first blade 612a and the second blade 612b, the cutting roll 600 may be configured with a single blade 612 extending along the CD direction for a length, L, on the outer circumferential surface 606. Although the cutting unit 500 is shown in FIG. 6 as cutting elastics in two elastic laminates 300, it should also be appreciated that the cutting unit 500 may be configured to cut elastics less than or more than two elastic laminates.

It is to be appreciated that the cutting unit 500 such as described above and as shown in FIG. 6 may include various blade assembly configurations, wherein the cutting units are configured with an interference distance between the anvil roll and the cutting roll 600 or the blades 612. Some example blade configurations are described in more detail below with reference to FIGS. 9A-11D. As discussed in more detail below, the interference distance causes distal edges 616 of the blades 612 to deflect when moving through the nip 603 between the anvil roll 602 and the cutting roll 600. As such, the deflection causes the distal edges 616 of the blades 612 exert pressure on the elastic laminates 300 advancing through the nip 603 and sever the elastics 302. As the cutting roll 600 continues to rotate and the blades 612 move away from the nip 603, the distal edges 616 of the blades 612 return to positions prior to being deflected upon entering the nip 603. As discussed in more detail below, the blade assemblies may configured in various ways to allow the distal edges 616 of the blades 612 to deflect. For example, in some embodiments, the blade assemblies may include blades that are adapted to bend or flex. In other embodiments, the blade may be connected with springs or other types of flexible supports that allow the distal edges of the blades to deflect. In yet other embodiments, the blade assemblies may include both flexible or bendable blades connected with springs or other types of flexible supports.

As previously discussed above and as shown in FIGS. 9A, 10A, and 11A, the cutting roll 600 is adjacent to the anvil roll 602 and create a nip 603 defined by a minimum distance, D, between the outer circumferential surface 606 of the cutting roll 602 and the outer circumferential surface 610 of the anvil roll 602. The blades 612 may extend radially outward from the outer circumferential surface 606 of the cutting roll 600 to the distal edge 616 by a distance, H. And the distance, H, of each blade 612 is greater than the distance, D, between the cutting roll 600 and the anvil roll 602, creating an interference distance between the distal edges 616 of the blades 612 and the outer circumferential surface 610 of the anvil roll 602. As such, in some embodiments the interference distance may be defined by the difference between the distance, H, and the distance, D. As shown in FIG. 8C, it is to be appreciated that the interference distance between the blade 612 and the anvil roll 602 for the apparatuses and methods herein may also be defined with reference to a distance, D1, and a distance, D2, wherein D2 is greater than D1. With continued reference to FIG. 8C, the distance, D1, is the minimum distance between the axis of rotation 604 of the cutting roll 600 and the outer circumferential surface 610 of the anvil roll 602. And the distance, D2, is the maximum distance between the axis of rotation 604 of the cutting roll 600 and the distal edge 616 of the blade 612. As such, the interference distance may be defined by the difference between the distance, D2, and the distance, D1. In some embodiments, the interference distance may be 5 µm or greater.

As shown in FIGS. 9A and 9B, the cutting unit 500 may include a blade assembly 622 having a blade 612 connected with a support member 624. In some embodiments, the support member 624 may be configured as a discrete piece that is releasably or permanently connected with cutting roll 600. In other embodiments, the support member 624 may configured as an integral part of the cutting roll 600. As shown in FIG. 9A, the support member 624 may include a first, base, portion 624a and a second, mounting, portion 624b. The mounting portion 624b may be connected with the base portion 624a to form a substantially L-shaped side view. As shown in FIG. 9B, the blade 612 may be connected with mounting portion 624b. Referring back to FIG. 9A, the blade 612 may extend radially outward from the support portion 624a of the support member 624 by a distance, H2. It is to be appreciated that the blade 612 may be releasably connected with the support member 624 in various ways, such as for example, with fasteners 626 in the form of bolts or screws. In some embodiments, the blade may be permanently connected with or made integral with the support member 624 or cutting roll 600.

With continued reference to FIG. 9A, as the blades 612 move though the nip 603 between the cutting roll 600 and the anvil roll 602, the interference distance may cause the blades 612 to flex or bend in a direction generally indicated by the arrow labeled as Dir1. As such, the distal edges 616 of the blades 612 may exert pressure on the elastic laminates 300 advancing through the nip 603 and sever the elastics 302 as discussed above. As the cutting roll 600 continues to rotate and the blades 612 move away from the nip 603 and returning to the original blade shapes before entering the nip 603 by flexing or bending back in a direction generally indicated by the arrow labeled as Dir2. It is to be appreciated that the forces the blade 612 exerts on the elastic laminate 300 advancing through the nip 603 may be affected by various parameters, such as for example: the blade material; the distance, H2, by which the blade extends from the base member; and the thickness, t, of the blade 612.

Figure 9E:
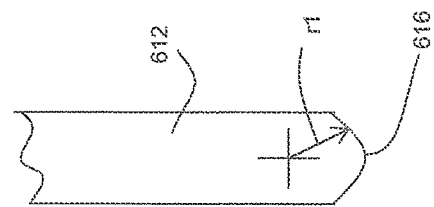
FIG. 9E is a detailed side view of a blade including a curved distal edge.
Figure 9D:
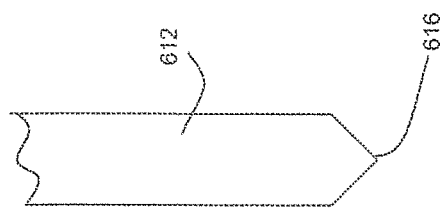
FIG. 9D is a detailed side view of a blade including a beveled distal edge.
Figure 9C:
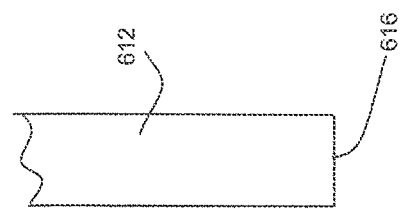
FIG. 9C is a detailed side view of a blade including a flat distal edge.

It is also to be appreciated that the blade 616 shown in FIGS. 9A and 9B may have differently shaped distal edges 616. For example, the blade 612 may include a flat distal edge 616, such as shown in FIG. 9C. In another example, the blade 616 may include a beveled distal edge 616, such as shown in FIG. 9D. And in yet another example, the blade 616 may include a curved distal edge 616, such as shown in FIG. 9E. The curved distal edge may be defined by a radius, r1. In some embodiments, the radius, r1, may be from about 50 µm to about 4000 µm.

FIGS. 10A and 10B show another embodiment of a blade assembly 622 that may be used with the cutting unit 500. As shown in FIGS. 10A and 10B, the blade assembly 622 may include a blade 612 connected with a support member 624. The blade assembly 622 may also include spring members 630 that connect the support member 624 with the cutting roll 602. As discussed below, the spring members 630 may compress and/or bend to allow the blade 612 to deflect when moving through the nip 603. As shown in FIGS. 10A-10C, the blade 612 may be cylindrically shaped and may be releasably connected with support member 624. The curved outer circumference of the cylindrically shaped blade may defined by a radius, r1, such as shown in FIG. 10C. In some embodiments, the radius, r1, may be from about 50 µm to about 4000 µm. It is also to be appreciated that the blade 616 shown in FIGS. 10A and 10B may have differently shaped distal edges 616, such as for example, a flat distal edge or a beveled distal edge.

With continued reference to FIG. 10A, as the blades 612 move though the nip 603 between the cutting roll 600 and the anvil roll 602, the interference distance may cause the spring members 630 to compress and/or bend, which in turn, allows the blades 612 to deflect in directions generally indicated by the arrows labeled as Dir1. As such, the compression and/or deformation of the spring members 630 causes the distal edges 616 of the blades 612 to exert pressure on the elastic laminates 300 advancing through the nip 603 and sever the elastics 302 as discussed above. As the cutting roll 600 continues to rotate and the blades 612 move away from the nip 603, the spring members 630 return to the original uncompressed states before entering the nip 603, which may cause the blades 612 to move in directions generally indicated by the arrows labeled as Dir2. It is to be appreciated that the forces the blade 612 exerts on the elastic laminate 300 advancing through the nip 603 may be affected by the spring constants and other parameters of the spring members 630. It is to be appreciated that the spring members 630 may be configured in various ways. For example, in some embodiments, the spring members 630 are configured as machined springs, such as for example, various types of machined springs available from Helical Products, Inc.

Figure 11A:
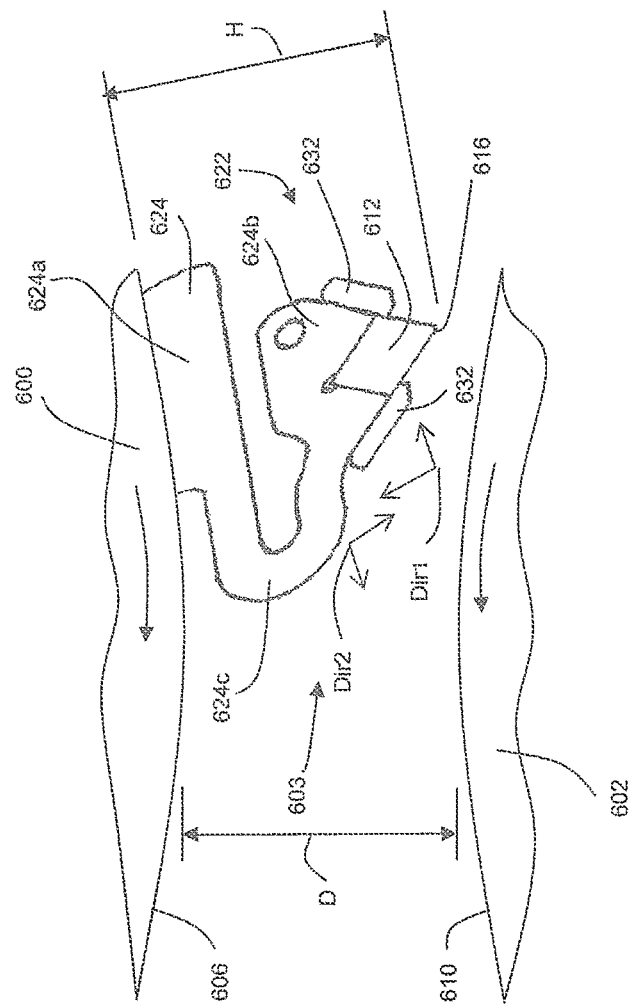
FIG. 11A is a detailed side view of a cutting apparatus and an embodiment of a blade assembly.
Figure 11B:
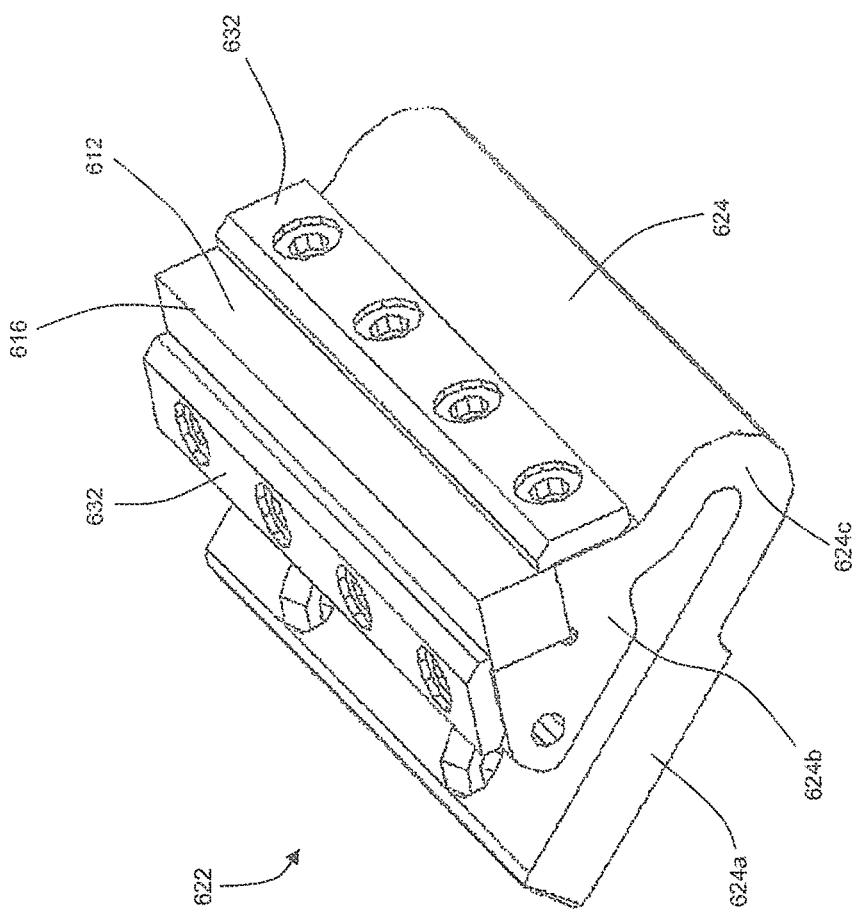
FIG. 11B is a detailed isometric view of the blade assembly of FIG. 11A.
Figure 11D:
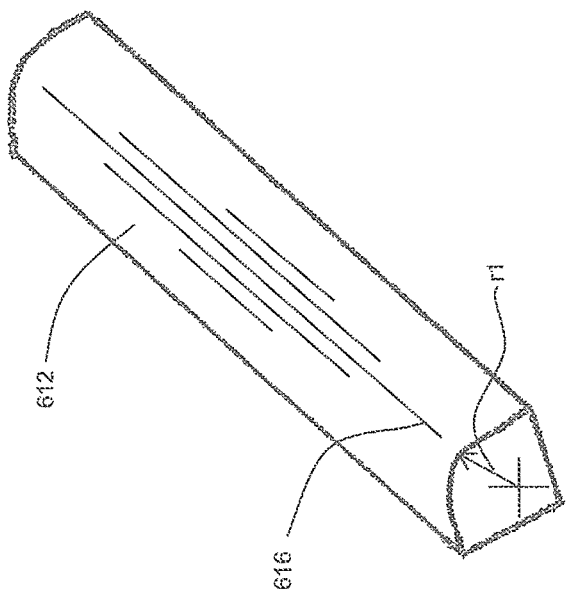
FIG. 11D is an isometric view of an embodiment of a blade having a curved distal edge.
Figure 11C:
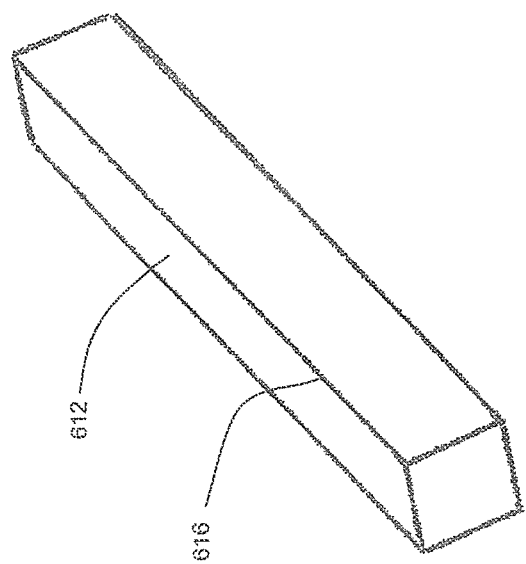
FIG. 11C is an isometric view of an embodiment of a blade having a beveled distal edge.
Figure 11E:
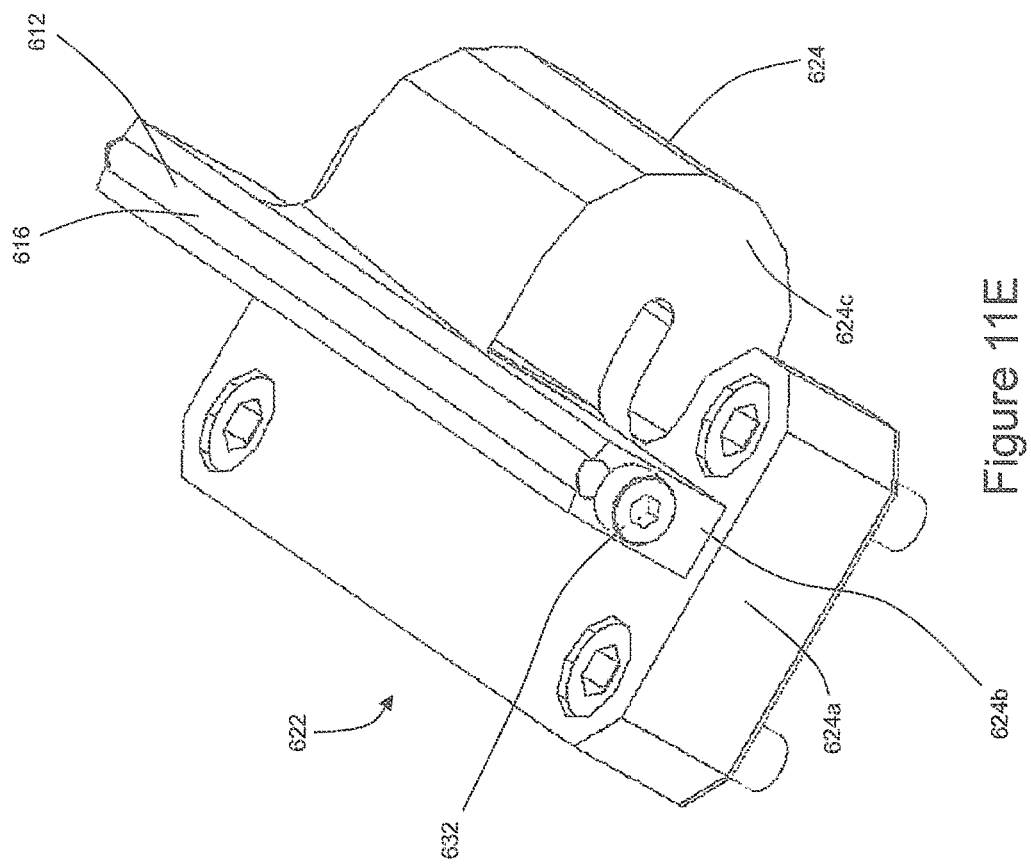
FIG. 11E is an isometric view of an embodiment a blade assembly having a support member that may be included with the blade assemblies of FIGS. 11A and 11B.

FIGS. 11A and 11B show yet another embodiment of a blade assembly 622 that may be used with the cutting unit 500. As shown in FIGS. 11A and 11B, the blade assembly 622 may include a blade 612 connected with a support member 624. The support member 624 may include a first, base, portion 624a; a second, mounting, portion 624b; and a third, flexible, flexile portion 624c. As illustrated, the flexible portion 624c connects the mounting portion 624b with the base portion 624a. The blade 612 may be positioned on mounting portion 624b and held in place with clamps 632 releasably connected with the mounting portion 624b. As discussed below, the flexible portion 624c of may flex and/or bend to allow the blade 612 to deflect when moving through the nip 603. As shown in FIGS. 11A-11C, the blade 612 may have a beveled distal edge 616. In another embodiment, such as shown in FIG. 11D, the blade 612 may have a curved distal edge 616 may defined by a radius, r1. In some embodiments, the radius, r1, may be from about 50 μm to about 4000 μm. In yet other embodiments, the support member 624 shown in FIGS. 11A and 11B may be adapted to hold a blade 612 that is cylindrically shaped, such as discussed above with reference to FIG. 10C. FIG. 11E shows a blade assembly 624 having a support member 624 with flexible portion 624c that is relatively narrower than the full length of the blade 612 as well as the first and second portions 624a, 624b, and as such, provides additional flexibility for severing elastics even there is misalignment between the knife roll and the anvil.

With continued reference to FIG. 11A, as the blades 612 move though the nip 603 between the cutting roll 600 and the anvil roll 602, the interference distance may cause the flexible portion 624c of the support member to flex or bend, which in turn, allows the blades 612 to deflect in directions generally indicated by the arrows labeled as Dir1. As such, the bending and/or deformation of the flexible portion 624c causes the distal edges 616 of the blades 612 to exert pressure on the elastic laminates 300 advancing through the nip 603 and sever the elastics 302 as discussed above. As the cutting roll 600 continues to rotate and the blades 612 move away from the nip 603, the flexible portions 624c of the support members 624 return to the original uncompressed states before entering the nip 603, which may cause the blades 612 to move back in directions generally indicated by the arrows labeled as Dir2. It is to be appreciated that the forces the blade 612 exerts on the elastic laminate 300 advancing through the nip 603 may be affected by the spring constants and other parameters of the flexible portion 624c of the support member 624.

It is to be appreciated that various embodiments of blade assembly configurations having flexible blades and/or flexible support members and/or springs have been disclosed herein. Such blade assembly configurations may provide relatively more simple machine design and fabrication requirements than those that may be required for other designs, such as rigid die cutter designs. For example, the presently disclosed blade assembly configurations may provide for greater flexibility in knife set-up and may reduce the level of precision that would otherwise be required for rigid die cutter configurations.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for severing elastic strands in an elastic laminate, the method comprising the steps of:
    advancing a continuous first substrate layer and a continuous second substrate layer in a machine direction;
    stretching a plurality of elastic strands in the machine direction;
    intermittently bonding the stretched plurality of elastic strands between the first substrate layer and the second substrate layer to form a continuous elastic laminate such that the elastic laminate includes bonded regions and non-bonded regions intermittently spaced along the machine direction, wherein the plurality of elastic strands are bonded to the first substrate layer and the second substrate layer in the bonded regions, and wherein the plurality of elastic strands are not bonded to the first substrate layer and the second substrate layer in the non-bonded regions;
    advancing the elastic laminate in the machine direction through a nip defined between a cutting roll and an anvil roll, the cutting roll rotating around a first axis of rotation and the anvil roll rotating around a second axis of rotation, wherein the anvil roll includes an outer circumferential surface defining a minimum distance D1 between the outer circumferential surface and first axis of rotation, wherein the cutting roll includes a blade having a distal edge defining a maximum distance D2 between the distal edge and the first axis of rotation, and wherein the D2 is greater than D1, wherein the distal edge of the blade defines a length that extends in a cross direction;
    deflecting the distal edge of the blade by an interference distance, wherein the interference distance is equal to or greater than a difference between D2 and D1; and
    severing the plurality of elastic strands by pressing the distal edge of the blade against the elastic laminate with the length of the distal edge extending across all the elastic strands in the non-bonded region in the nip without cutting either the continuous first substrate layer or the continuous second substrate layer.

2. The method of claim 1, wherein the step of deflecting the distal edge of the blade further comprises bending the blade.

3. The method of claim 1, wherein the distal edge of the blade is curved.

4. The method of claim 3, wherein the curved distal edge is defined by a radius of about 50 μm to about 4000 μm.

5. The method of claim 1, wherein the blade is connected with a support member.

6. The method of claim 5, wherein the support member is connected with a spring, and the spring is connected with the cutting roll, and wherein the step of deflecting the distal edge of the blade further comprises compressing the spring.

7. The method of claim 6, wherein the step of deflecting the distal edge of the blade further comprises bending the spring.

8. The method of claim 5, wherein the step of deflecting the distal edge of the blade further comprises bending the support member.

9. The method of claim 1, wherein the interference distance is at least 5 μm.

10. The method of claim 1, further comprising the step of bonding the continuous first substrate layer to the continuous second substrate layer with the distal edge of the blade.

\* \* \* \* \*